US008603171B2

(12) United States Patent
McClellan, III et al.

(10) Patent No.: US 8,603,171 B2
(45) Date of Patent: Dec. 10, 2013

(54) SPINAL DISC IMPLANTS WITH FLEXIBLE KEELS AND METHODS OF FABRICATING IMPLANTS

(75) Inventors: John W. McClellan, III, Omaha, NE (US); Guilhem Denoziere, Atlanta, GA (US); Rebeccah Brown, Decatur, GA (US); Matthew Miller, Tampa, FL (US)

(73) Assignee: MiMedx Group, Inc., Marietta, GA (US)

( * ) Notice: Subject to any disclaimer, the term of this patent is extended or adjusted under 35 U.S.C. 154(b) by 1794 days.

(21) Appl. No.: 11/626,401

(22) Filed: Jan. 24, 2007

(65) Prior Publication Data

US 2007/0179621 A1     Aug. 2, 2007

Related U.S. Application Data

(60) Provisional application No. 60/761,902, filed on Jan. 25, 2006.

(51) Int. Cl.
*A61F 2/44* (2006.01)

(52) U.S. Cl.
USPC ..................................... 623/17.16

(58) Field of Classification Search
USPC ........................... 623/17.11–17.16
See application file for complete search history.

(56) References Cited

U.S. PATENT DOCUMENTS

| 3,673,612 A | 7/1972 | Merrill et al. |
| 4,472,542 A | 9/1984 | Nambu |
| 4,664,857 A | 5/1987 | Nambu |
| 4,734,097 A | 3/1988 | Tanabe et al. |
| 4,759,766 A | 7/1988 | Büttner-Janz et al. |
| 5,106,876 A | 4/1992 | Kawamura |
| 5,141,973 A | 8/1992 | Kobayashi et al. |
| 5,258,043 A | 11/1993 | Stone |
| 5,288,503 A | 2/1994 | Wood et al. |
| 5,314,477 A | 5/1994 | Marnay |
| 5,336,551 A | 8/1994 | Graiver et al. |
| 5,346,935 A | 9/1994 | Suzuki et al. |
| 5,401,269 A | 3/1995 | Büttner-Janz et al. |
| 5,458,643 A * | 10/1995 | Oka et al. ............... 623/17.16 |
| 5,522,898 A | 6/1996 | Bao |
| 5,556,431 A | 9/1996 | Büttner-Janz |
| 5,981,826 A | 11/1999 | Ku et al. |
| 6,045,552 A * | 4/2000 | Zucherman et al. ........ 606/86 B |
| 6,093,205 A * | 7/2000 | McLeod et al. .......... 623/17.16 |

(Continued)

FOREIGN PATENT DOCUMENTS

| EP | 0346129 A | 12/1989 |
| EP | 0505634 | 9/1992 |

(Continued)

OTHER PUBLICATIONS

International Search Report dated Jul. 27, 2007 for corresponding PCT application No. PCT/US2007/001933.

(Continued)

*Primary Examiner* — Ellen C Hammond
(74) *Attorney, Agent, or Firm* — Myers Bigel Sibley & Sajovec, P.A.

(57) ABSTRACT

Spinal disc and other implants include at least one flexible keel that extends substantially outwardly, typically upwardly or downwardly, beyond the primary body of the implant. Methods of fabricating elastomeric implants using a mold are also described.

32 Claims, 18 Drawing Sheets

(56) References Cited

U.S. PATENT DOCUMENTS

| | | |
|---|---|---|
| 6,102,954 A | 8/2000 | Albrektsson et al. |
| 6,231,605 B1 | 5/2001 | Ku |
| 6,268,405 B1 | 7/2001 | Yao et al. |
| 6,686,437 B2 | 2/2004 | Buchman et al. |
| 6,740,118 B2 | 5/2004 | Eisermann et al. |
| 6,802,863 B2 | 10/2004 | Lawson et al. |
| 6,827,743 B2 | 12/2004 | Eisermann et al. |
| 6,936,071 B1 * | 8/2005 | Marnay et al. ............. 623/17.15 |
| 6,960,617 B2 | 11/2005 | Omidian et al. |
| 7,048,766 B2 | 5/2006 | Ferree |
| 7,060,097 B2 | 6/2006 | Fraser et al. |
| 7,066,960 B1 | 6/2006 | Dickman |
| 7,083,649 B2 | 8/2006 | Zucherman et al. |
| 2002/0077701 A1 | 6/2002 | Kuslich |
| 2003/0008396 A1 | 1/2003 | Ku |
| 2003/0176922 A1 | 9/2003 | Lawson et al. |
| 2004/0059425 A1 | 3/2004 | Schmieding |
| 2004/0073312 A1 | 4/2004 | Eisermann et al. |
| 2004/0093087 A1 * | 5/2004 | Ferree et al. ............... 623/17.13 |
| 2004/0117022 A1 | 6/2004 | Marnay et al. |
| 2004/0143329 A1 | 7/2004 | Ku |
| 2004/0172135 A1 | 9/2004 | Mitchell |
| 2004/0220670 A1 | 11/2004 | Eisermann et al. |
| 2004/0249465 A1 | 12/2004 | Ferree |
| 2005/0043733 A1 | 2/2005 | Eisermann et al. |
| 2005/0043802 A1 | 2/2005 | Eisermann et al. |
| 2005/0055099 A1 * | 3/2005 | Ku ............................. 623/17.16 |
| 2005/0071003 A1 | 3/2005 | Ku |
| 2005/0106255 A1 | 5/2005 | Ku |
| 2005/0149196 A1 | 7/2005 | Zucherman et al. |
| 2005/0154462 A1 | 7/2005 | Zucherman et al. |
| 2005/0171608 A1 | 8/2005 | Peterman et al. |
| 2005/0222683 A1 * | 10/2005 | Berry ........................ 623/17.13 |
| 2005/0287187 A1 | 12/2005 | Mansmann |
| 2006/0036322 A1 * | 2/2006 | Reiley ....................... 623/17.11 |
| 2006/0265075 A1 | 11/2006 | Baumgartner et al. |
| 2007/0179622 A1 | 8/2007 | Denoziere et al. |
| 2008/0174043 A1 | 7/2008 | Denoziere et al. |

FOREIGN PATENT DOCUMENTS

| | | | | |
|---|---|---|---|---|
| EP | 0919209 | | 6/1999 | |
| WO | WO 93/16664 A | | 9/1993 | |
| WO | WO 99/00074 | * | 1/1999 | ............... A61F 2/44 |
| WO | WO 0122902 | | 4/2001 | |
| WO | WO 2005/097006 A | | 10/2005 | |

OTHER PUBLICATIONS

Stauffer et al. "Poly (vinyl alcohol) hydrogels prepared by freezing—thawing cyclic processing" *Polymer* 33(1818):3932-3936 (1992).

* cited by examiner

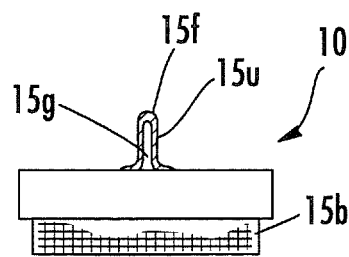 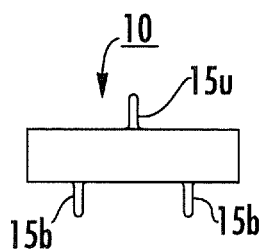
FIG. 4A  FIG. 4B
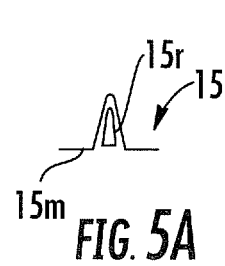 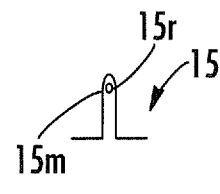 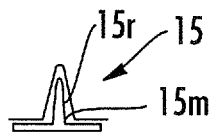
FIG. 5A  FIG. 5B  FIG. 5C
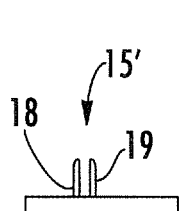 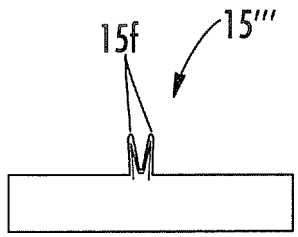 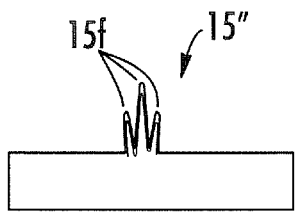
FIG. 6A  FIG. 6B  FIG. 6C
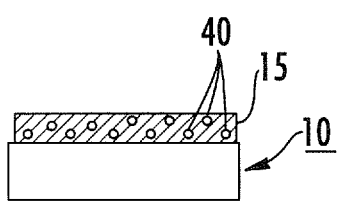 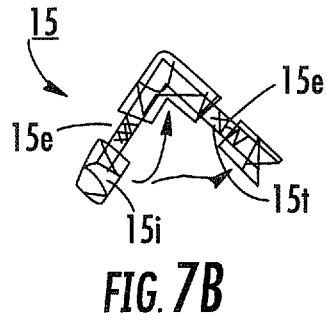 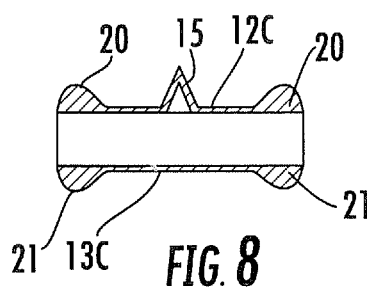
FIG. 7A  FIG. 7B  FIG. 8
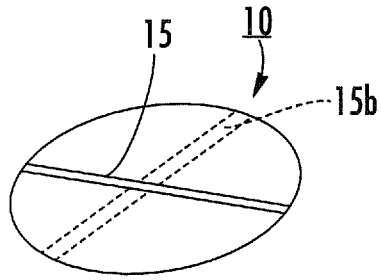 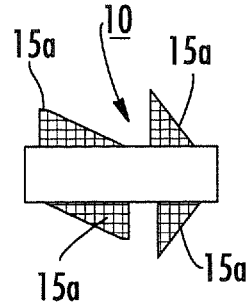 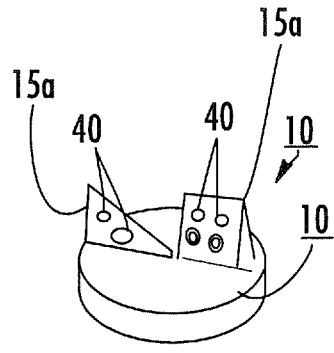
FIG. 9  FIG. 10A  FIG. 10B

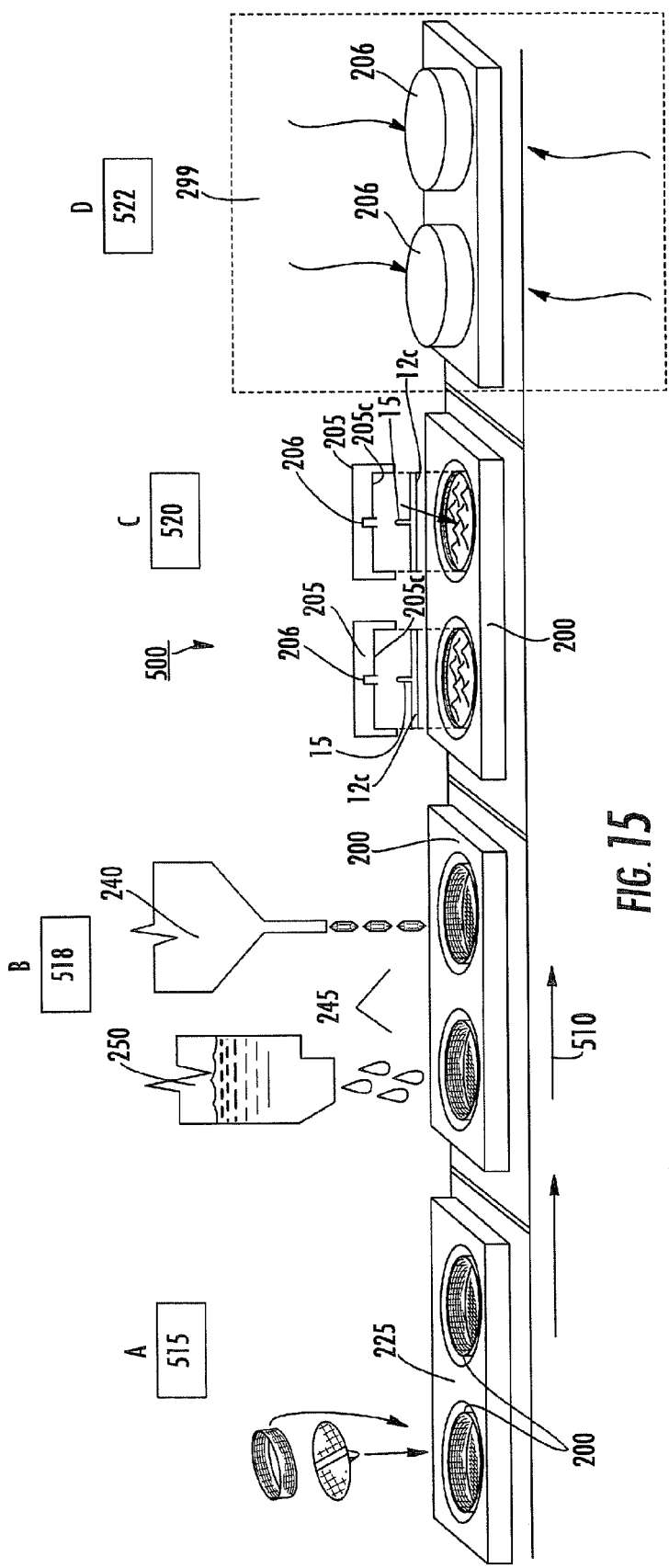

SPINAL DISC IMPLANTS WITH FLEXIBLE KEELS AND METHODS OF FABRICATING IMPLANTS

RELATED APPLICATIONS

This application claims priority to U.S. Provisional Application Ser. No. 60/761,902, filed Jan. 25, 2006, the entire contents of the above-referenced documents are hereby incorporated herein by reference as if recited in full herein.

FIELD OF THE INVENTION

The invention relates to implants and may be particularly relevant to spinal total disc replacement (TDR) implants.

BACKGROUND OF THE INVENTION

The vertebrate spine is made of bony structures called vertebral bodies that are separated by relatively soft tissue structures called intervertebral discs. The intervertebral disc is commonly referred to as a spinal disc. The spinal disc primarily serves as a mechanical cushion between the vertebral bones, permitting controlled motions between vertebral segments of the axial skeleton. The disc acts as a joint and allows physiologic degrees of flexion, extension, lateral bending, and axial rotation. The disc must have sufficient flexibility to allow these motions and have sufficient mechanical properties to resist the external forces and torsional moments caused by the vertebral bones.

The normal disc is a mixed avascular structure having two vertebral end plates ("end plates"), an annulus fibrosis ("annulus") and a nucleus pulposus ("nucleus"). Typically, about 30-50% of the cross sectional area of the disc corresponds to the nucleus. Generally described, the end plates are composed of thin cartilage overlying a thin layer of hard, cortical bone that attaches to the spongy cancellous bone of the vertebral body. The end plates act to attach adjacent vertebrae to the disc.

The annulus of the disc is a relatively tough, outer fibrous ring. For certain discs, particularly for discs at lower lumar levels, the annulus can be about 10 to 15 millimeters in height and about 10 to 15 millimeters in thickness, recognizing that cervical discs are smaller.

Inside the annulus is a gel-like nucleus with high water content. The nucleus acts as a liquid to equalize pressures within the annulus, transmitting the compressive force on the disc into tensile force on the fibers of the annulus. Together, the annulus and nucleus support the spine by flexing with forces produced by the adjacent vertebral bodies during bending, lifting, etc.

The compressive load on the disc changes with posture. When the human body is supine, the compressive load on the third lumbar disc can be, for example, about 200 Newtons (N), which can rise rather dramatically (for example, to about 800 N) when an upright stance is assumed. The noted load values may vary in different medical references, typically by about +/−100 to 200 N. The compressive load may increase, yet again, for example, to about 1200 N, when the body is bent forward by only 20 degrees.

The spinal disc may be displaced or damaged due to trauma or a degenerative process. A disc herniation occurs when the annulus fibers are weakened or torn and the inner material of the nucleus becomes permanently bulged, distended, or extruded out of its normal, internal annular confines. The mass of a herniated or "slipped" nucleus tissue can compress a spinal nerve, resulting in leg pain, loss of muscle strength and control, even paralysis. Alternatively, with discal degeneration, the nucleus loses its water binding ability and deflates with subsequent loss in disc height. Subsequently, the volume of the nucleus decreases, causing the annulus to buckle in areas where the laminated plies are loosely bonded. As these overlapping plies of the annulus buckle and separate, either circumferential or radial annular tears may occur, potentially resulting in persistent and disabling back pain. Adjacent, ancillary facet joints will also be forced into an overriding position, which may cause additional back pain. The most frequent site of occurrence of a herniated disc is in the lower lumbar region. The cervical spinal disks are also commonly affected.

There are several types of treatment currently being used for treating herniated or degenerated discs: conservative care, discectomy, nucleus replacement, fusion and prosthesis total disc replacement (TDR). It is believed that many patients with lower back pain will get better with conservative treatment of bed rest. For others, more aggressive treatments may be desirable.

Discectomy can provide good short-term results. However, a discectomy is typically not desirable from a long-term biomechanical point of view. Whenever the disc is herniated or removed by surgery, the disc space will narrow and may lose much of its normal stability. The disc height loss may cause osteo-arthritis changes in the facet joints and/or compression of nerve roots over time. The normal flexibility of the joint is lost, creating higher stresses in adjacent discs. At times, it may be necessary to restore normal disc height after the damaged disc has collapsed.

Fusion is a treatment by which two vertebral bodies are fixed to each other by a scaffold. The scaffold may be a rigid piece of metal, often including screws and plates, or allo or auto grafts. Current treatment is to maintain disc space by placement of rigid metal devices and bone chips that fuse two vertebral bodies. The devices are similar to mending plates with screws to fix one vertebral body to another one. Alternatively, hollow metal cylinders filled with bone chips can be placed in the intervertebral space to fuse the vertebral bodies together (e.g., LT-Cage™ from Sofamor-Danek or Lumbar I/F CAGE™ from DePuy). These devices have disadvantages to the patient in that the bones are fused into a rigid mass with limited, if any, flexible motion or shock absorption that would normally occur with a natural spinal disc. Fusion may generally eliminate symptoms of pain and stabilize the joint. However, because the fused segment is fixed, the range of motion and forces on the adjoining vertebral discs can be increased, possibly enhancing their degenerative processes.

Some recent TDR devices have attempted to allow for motion between the vertebral bodies through articulating implants that allow some relative slippage between parts (e.g., ProDisc®, Charite™), see, for example, U.S. Pat. Nos. 5,314,477, 4,759,766, 5,401,269 and 5,556,431. As an alternative to the metallic-plate, multi-component TDR (total disc replacement) designs, a flexible solid elastomeric spinal disc implant that is configured to simulate natural disc action (i.e., can provide shock absorption and elastic tensile and compressive deformation) is described in U.S. Patent Application Publication No. 2005/0055099 to Ku, the contents of which are hereby incorporated by reference as if recited in full herein.

SUMMARY OF EMBODIMENTS OF THE INVENTION

Embodiments of the invention are directed to spinal implants with flexible keels.

Other embodiments are directed to methods of fabricating flexible spinal disc implants with flexible keels and/or fabrication molds therefor.

The flexible keels can comprise a biocompatible mesh material such as a polyester fabric and the TDR spinal implants may further comprise a crystalline poly(vinyl alcohol) (PVA) hydrogel. In some embodiments, the flexible keels can include a plurality of spaced apart bone/tissue in-growth apertures. The flexible keels can be configured to bend (slightly) and/or move side-to-side while having sufficient rigidity to maintain a generally upwardly or downwardly extending orientation outside the body.

Other embodiments are directed to spinal implant fabrication molds. The molds include: (a) a mold having a three-dimensional shape substantially corresponding to that of a natural spinal disc, the mold having a cavity with an upstanding sidewall, a floor and a ceiling; (b) at least one mesh liner with an outwardly extending region (such as a fold region) in the mold (which can optionally be a unitary layer or multiple layers configured to substantially cover the floor and the upstanding sidewall); and (c) a quantity of polyvinyl alcohol materials and irrigation fluid disposed in the mold over the at least one liner to form a hydrogel implant body. During exposure to heat, the liner integrally attaches to a molded spinal disc prosthesis comprising the hydrogel.

Other embodiments are directed to spinal implant fabrication molds that include: (a) a mold having a cavity with an upstanding sidewall, a floor and a ceiling, the mold further comprising at least one elongate aperture or channel extending outwardly along the floor of the mold; (b) a layer of biocompatible porous material disposed in the mold such that a segment (typically fold) of the material extends through the at least one floor aperture or into the floor channel; and (c) a quantity of biocompatible moldable material disposed in the mold over the layer of porous material having a fluid volume sufficient to fill the mold to a desired level. During molding, the moldable material is configured to form a solid spinal implant body with the layer of porous material being integrally attached thereto so as to define a flexible keel.

Yet other embodiments are directed to method of fabricating implantable total disc replacement spinal disc prosthesis. The methods include: (a) placing an inferior mesh layer with a generally downwardly extending fold region on a floor of a bottom member of a three-dimensional mold such that the fold extends through a receiving aperture in the floor; (b) placing an annular mesh layer against an upstanding sidewall of the mold; (c) forming a generally outwardly extending elongate segment with an open center space in the inferior and superior mesh layers before or during the respective placing steps; (d) introducing moldable material into the mold so that the material covers the inferior and annular mesh layers; (e) placing a superior mesh layer with a generally upwardly extending segment region over the moldable material; (f) placing a top member on the bottom member to close the mold; and (g) heating to a desired temperature so that the mold holding the moldable material is heated to at least about 80° C. for a target time; then (h) forming a molded spinal implant body formed by the heated moldable material whereby the mesh layers are integrally attached to the molded body formed by the moldable material.

Some embodiments of the invention are directed to methods of fabricating an implantable total disc replacement spinal disc prosthesis that include: (a) molding an elastomeric primary body of an implant into a desired implant shape; and (b) attaching at least one flexible keel to the molded implant so that the at least one flexible keel extends outwardly from at least one of a superior or inferior primary surface of the molded implant.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 4A is a front schematic view of another embodiment of a spinal disc implant according to embodiments of the present invention.

FIG. 4B is a front schematic view of another embodiment of a spinal disc implant according to embodiments of the present invention.

FIGS. 5A-5C are cross-sectional views of a keel with reinforcement material according to embodiments of the present invention.

FIGS. 6A-6C are front or side schematic views of other embodiments of different configurations of flex-keels for a spinal disc implant according to embodiments of the present invention.

FIG. 7A is a front or side schematic view of another embodiment of a spinal disc implant according to embodiments of the present invention.

FIG. 7B is an enlarged partial view of the keel shown in FIG. 7A, illustrating locally exposed regions of mesh according to some embodiments of the present invention.

FIG. 8 is a schematic front or side view of another embodiment of a spinal disc implant according to embodiments of the present invention.

FIG. 9 is a schematic top view of another embodiment of a spinal disc implant according to embodiments of the present invention.

FIG. 10A is a schematic side or front view of yet another embodiment of a spinal disc implant according to embodiments of the present invention.

FIG. 10B is a side perspective view of yet another spinal disc implant according to embodiments of the present invention.

FIG. 15 is a schematic illustration of a semi-automated assembly line that can be used to fabricate spinal disc implants according to embodiments of the present invention.

FIG. 16A is a cross-sectional view of a spinal disc implant mold according to embodiments of the present invention.

FIG. 16B is a bottom view of a spinal disc implant mold according to embodiments of the present invention.

FIG. 16C is a bottom view of a spinal disc implant mold according to embodiments of the present invention.

DETAILED DESCRIPTION

Figure 1A:
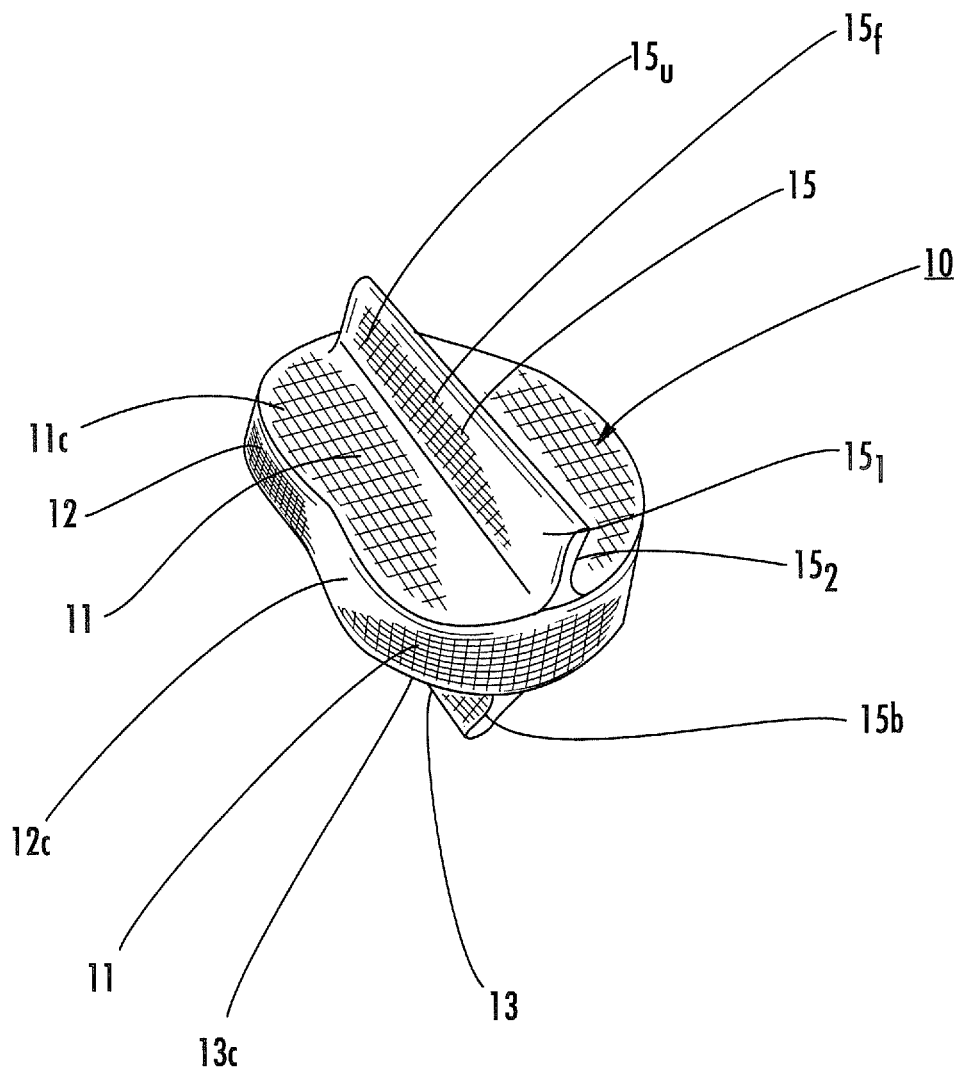
FIG. 1A is a top perspective view of implantable spinal disc prosthesis with flexible keels according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "spinal disc implant" and "spinal disc prosthesis" are used interchangeably herein to designate total disc replacements using an implantable total spinal disc replacement prosthesis (rather than a nucleus only) and as such are configured to replace the natural spinal disc of a mammalian subject (for veterinary or medical (human) applications). In contrast, the term "spinal implant" refers to both TDR spinal disc implants and alternative spinal implants, such as, for example, a spinal annulus or a spinal nucleus implant.

The term "flexible" means that the member can be flexed or bent. In some embodiments, the keel is flexible but has sufficient rigidity to be substantially self-supporting so as to be able to substantially maintain a desired configuration outside of the body. The keel can include reinforcement to increase its rigidity.

The term "keel" means an implant component, feature or member that is configured to be received in a recess or mortise in an adjacent bone to facilitate short and/or long-term fixation and/or to provide twist or torsion resistance in situ. The term "keel" also includes a discontinuous keel configuration and/or a keel configuration that does not extend the entire length of the implant body, such as one or more axially aligned or offset keels as shown, for example, in FIG. 10A.

The term "mesh" means any flexible material in any form including, for example, knotted, braided, extruded, stamped, knitted, woven or otherwise, and may include a material with a substantially regular foramination pattern and/or irregular foramination patterns.

The term "macropores" refers to apertures having at least about a 0.5 mm diameter or width size, typically a diameter or width that is between about 1 mm to about 3 mm, and more typically a diameter or width that is between about 1 mm to about 1.5 mm (the width dimension referring to non-circular apertures). Where mesh keels are used, the macropores are larger than the openings or foramina of the mesh substrate. The macropores may promote bony through-growth for increased fixation and/or stabilization over time.

The term "loop" refers to a shape in the affected material that has a closed or nearly closed turn or figure. For example, the loop can have its uppermost portion merge into two contacting lower portions or into two proximately spaced apart lower portions. The term "fold" means to bend over and the bend of the fold may have a sharp or rounded edge. The terms "pleat" or "fold" refer to doubling material on itself (with or without sharp edges).

FIG. 1A illustrates one embodiment of spinal disc implant 10. The implant 10 can include at least one keel 15 on at least one primary surface. As shown, the implant 10 includes at least one flexible keel 15. In this embodiment, the flexible keel 15 is an anterior/posterior keel. In the embodiment shown in FIGS. 1A and 1B, the implant 10 includes both upper and lower keels 15u, 15b on respective superior and inferior primary surfaces. In the embodiment shown in FIG. 1B, the keel 15 can be oriented to run substantially laterally.

Other keel orientations and configurations may also be used. For example, FIG. 4A illustrates that the upper keel 15u can extend a first direction (such as anteriorly/posteriorly) and the bottom keel 15b can extend in another direction (such as laterally). FIG. 4B illustrates that one primary surface (shown as the inferior surface) can have a lesser number of keels 15. FIG. 9 illustrates that the keel 15 can be oblique or angled. The keel 15 can extend a distance outward from the implant body between about 2 to about 15 mm, typically between about 5-10 mm. The flexible keel 15 may provide twist or torsion resistance for the implant 10 and/or facilitate short and long term fixation. In some embodiments, the keel 15 can comprise a material with a thickness between about 0.1-5 mm, typically between about 0.5-3 mm, and more typically between about 1-2 mm.

FIGS. 5A-5C illustrate that the flex keel 15 can include structural reinforcement 15r. The reinforcement 15r can include, for example, coatings, materials or components that add rigidity to the keel 15. The reinforcement can be applied to an outer portion and/or inner portion of the keel 15. As shown in FIG. 5A, an increased rigidity member 15m, which can be a polymer or metallic mesh or solid member that resides in an interior portion of the keel 15. In some embodiments, the member 15m is a discrete hydrogel insert 15i (FIGS. 14B, 14C) that can be inserted into the keel 15 or the keel can be folded about the insert 15m. In some embodiments, the insert 15m can be a hydrogel insert, typically between about 0.5-1 mm thick that resides between the two segments of mesh forming the keel 15. The mesh/insert subassembly is then used into the casting/molding process as described further below. This mesh insert can be used to ensure a proper filling of the keel cavity with hydrogel in order to sufficiently embed the mesh material.

FIG. 5B illustrates that the reinforcement 15r can include a discrete member 15m that resides at an upper portion of the keel 15. A pocket can be formed in the keel to maintain the desired location therein (top-to-bottom and/or end-to-end). Additional discrete or attached longitudinally spaced members can also be used (not shown). FIG. 5C illustrates that the reinforcement 15r can be a member 15m that is molded into the implant body to extend into the keel interior.

Figure 1B:
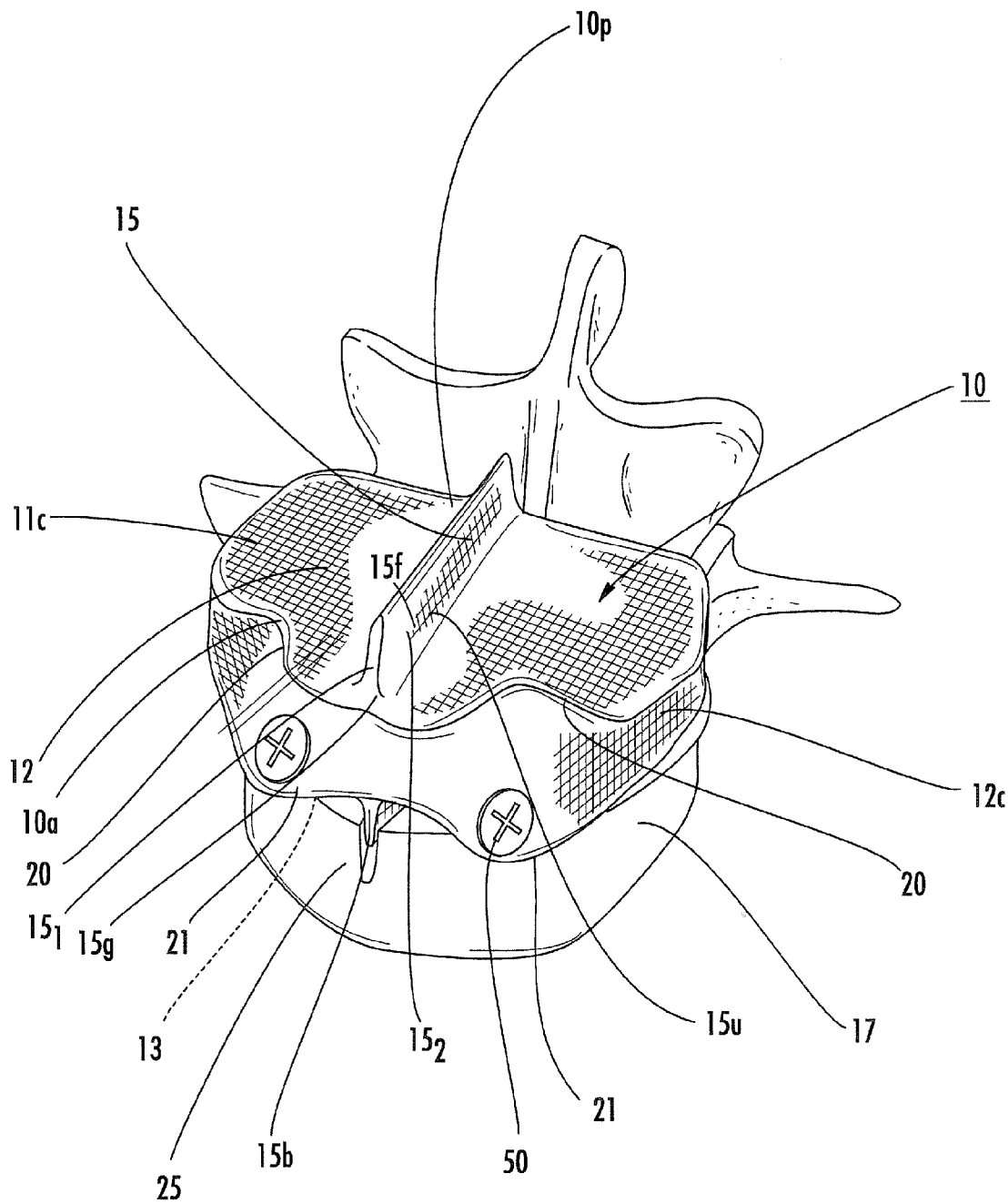
FIG. 1B is a top perspective view of another implantable spinal disc prosthesis with flexible keels according to embodiments of the present invention.
Figure 1C:
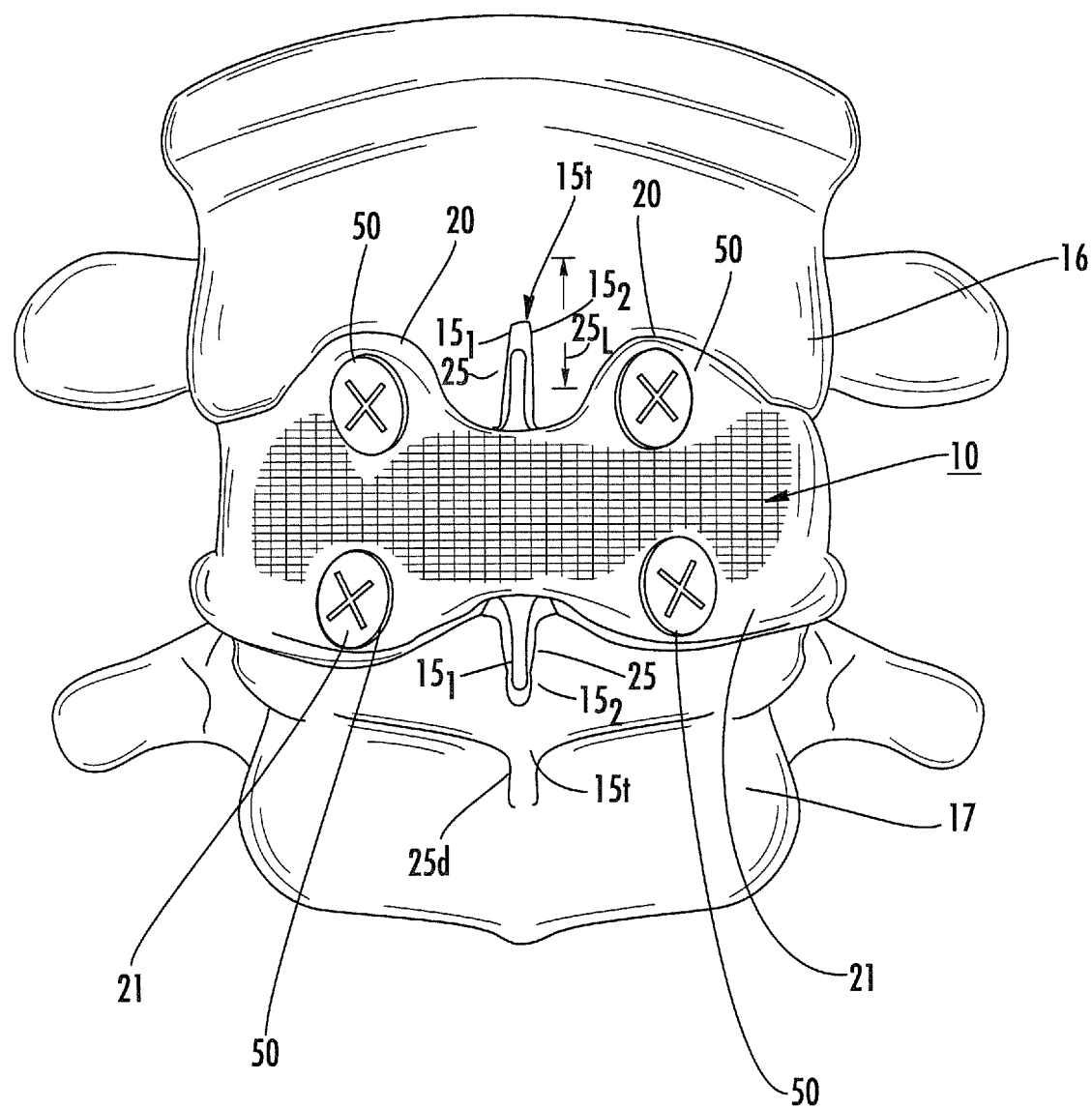
FIG. 1C is a front view of the spinal disc prosthesis shown in FIG. 1B in position with the flexible keels in respective receiving mortises formed in adjacent vertebrae according to embodiments of the present invention.

As shown in FIGS. 1B and 1C, the keel 15 is configured to enter a respective channel or mortise 25 formed in an adjacent vertebrae. The channel 25 can have a relatively shallow depth 25d that is greater than the height of the keel 15. In some embodiments, the channel 25 can have a depth $25_L$ that is between about 5-12 mm.

As described above, the implant 10 can include at least one flexible keel 15 extending from at least one surface. In some embodiments, the implant can include a plurality of keels from one or mores surfaces (see, e.g., FIG. 4B) and the implant 10 can include the same number of keels 15 extending from each primary surface or different numbers of keels 15 extending from each primary surface. The flexible keel(s) 15 can be porous, and in particular embodiments, can comprise a biocompatible elastomeric, typically polymer, mesh material. In the embodiments shown in FIGS. 1A-1C, 2A, 2B and 3A, the keel 15 is formed by a substantially outwardly extending (generally upwardly extending for the upper keel 15u) fold 15f formed in a unitary porous, typically mesh, material layer 10m.

FIGS. 1A-1C, 2A, 2B, 3A and 3B, show the implant 10 can include at least one porous mesh material layer 10m, shown as including three discrete layers 11, 12, 13 that can be moldably attached to a primary molded body 10b. In the embodiment shown, the mesh layers 10m include superior and inferior primary surface mesh-covering layers 11, 13, respectively and an annulus surface mesh-covering layer 12. The annulus layer 12 can be formed as a continuous or seamed ring to radial and/or axial expansion of the body 10b. In other embodiments, the annulus cover layer 12 can be discontinuous about the molded primary body 10b.

Similarly, the mesh 10m can be of any suitable biocompatible material. Where mesh layers 10m are used on more than one surface, the different mesh layers may be of different mesh material, thickness and/or mesh porosity. As shown, in FIGS. 2A and 2B, the endplate mesh layers 11, 13 may have a different mesh pattern than the annular (peripheral) mesh ring 12, with the peripheral mesh ring 12 having smaller pore sizes from that of the endplate mesh layers 11, 13. The pore dimensions of the superior/inferior (e.g., endplate) mesh layers 11, 13 can be selected to promote tissue in-growth. Exemplary pore sizes for tissue ingrowth and/or bone ingrowth into the exposed mesh scaffold of the endplate mesh layers 11, 13 is typically between about 0.5 mm to about 1 mm. Smaller pore sizes may be used on the annular mesh layer 12, typically between about 0.1 mm to about 0.5 mm as this mesh 12 may not be exposed (e.g., is substantially encapsulated in the mold material) and has a desired strength related to mesh density. The mesh layers 11, 13 can be any suitable thickness and pore pattern configured to promote tissue in-growth, and may typically be between about 0.5 mm to about 5 mm thick, more typically between about 0.7 mm to about 2 mm thick, such as about 0.75 mm thick.

In some embodiments, the mesh layers 10m can all be polyester mesh layers that may be extruded, knitted, braided, woven or otherwise formed into a mesh pattern. In some embodiments, the mesh comprises a multi-filament fiber(s) that can provide increased strength over conventional polyester material. For example, at least one of the layers 11, 12, 13, such as, for example, the annular mesh 12, can comprise yarns of a polyester mesh multifilament fiber that, for example, can be made out of a High Tenacity Polyester Teraphthalate (HTPET), which typically has a longer molecular chain than conventional polyester material, therefore providing more strength to the mesh than a regular polyester material. In particular embodiments, all the mesh layers 11, 12, 13 comprise HTPET. However, it is noted that the structure (density) of different mesh layers or regions may vary slightly due to strength, flexibility, exposed mesh, tissue ingrowth and other factors. In some embodiments, the mesh can be a high strength mesh that using a ball burst test (ref. ASTM D3787-01), can have a burst value between about 1500-3000 N and also a slope of the linear portion of the load/displacement curve of between about 150-300 N/mm. In other embodiments, one or more of the mesh layers 11, 12, 13 can include a polyester mesh of about 0.7 mm thick that is similar to or the same as that available as Fablok Mills Mesh #9464 from Fablok Mills, Inc., located in Murray Hill, N.J.

Figure 3A:
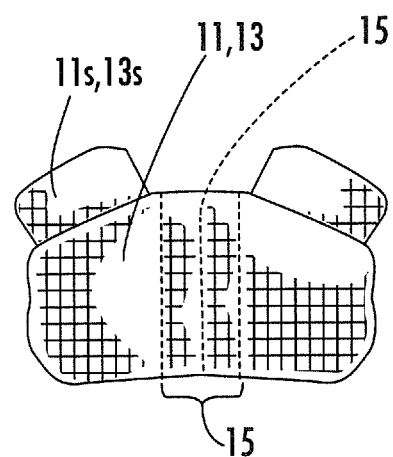
FIG. 3A is a top view of a superior/inferior mesh layer that can be used to form the keel for the implant shown in FIG. 2A according to embodiments of the invention.
Figure 3B:
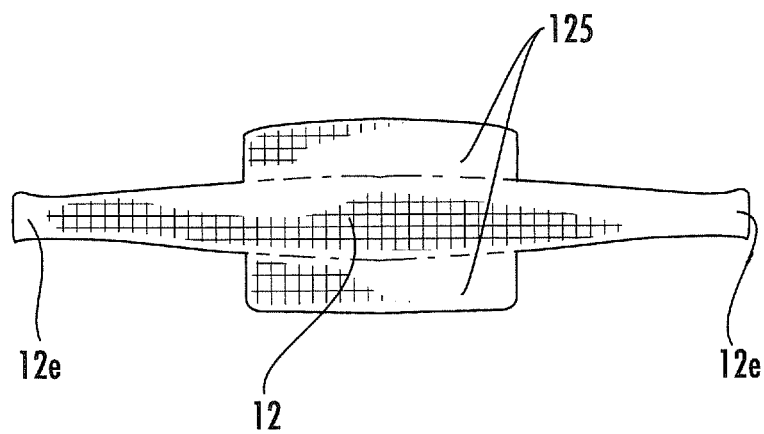
FIG. 3B is a top view of an annular mesh layer that can be used to form the implant shown in FIG. 3A according to embodiments of the invention.

FIGS. 3A and 3B illustrate exemplary configurations of the different mesh pieces 11, 12, 13. FIG. 3B illustrates the peripheral (annulus) mesh ring 12 and FIG. 3A illustrates examples the top and bottom end plate mesh pieces 11, 13. The top and bottom end plate pieces 11, 13 are typically the same or substantially similar, the endplate geometry may vary slightly due to different convexivity of the endplates. As shown, the ends 12e of the peripheral mesh ring can be detached until molded to the implant body as an outer ring. However, in an alternative design, the peripheral mesh ring is a continuous tube or ring member. The ring with the molded polymer body 10b can limit radial expansion of the body 10b in situ. The flexibility of the molded body 10b and integrally attached peripheral mesh ring 12 may allow some limited radial expansion.

As shown in FIGS. 2A, 2B, 3A and 3B, the implant 10 can use a continuation or extension of each of the three pieces of mesh material 11s, 12s, 13s to form a skirt 14 (which can also be described as a tab) reinforced with the molded material, to provide a means for attaching to vertebral bodies. FIG. 1B illustrates the implant with bone attachment tab extensions 21, that may be formed using outer portions of the respective mesh layers 11, 12, and/or 12, 13 meeting to embed with molded material. In particular embodiments, the skirt 14 and/or extensions 21, can be between about 1-4 mm thick, typically about 2 mm thick. For the latter, each of the mesh layers can be about 0.75 mm thick. The additional thickness of the skirt 14 (or extensions 21,) is due to the mold material that covers and embeds the layers forming the skirt material 14. None of the mesh layers are required to extend over edges or corners and the mesh is not required to encapsulate the molded body.

The endplate mesh layers 11, 13 may restrain the expansion of the body 10b to some extent in the radial direction, but typically not in the axial direction. The peripheral mesh ring 12 may slightly restrain the primary molded body 10b (e.g., PVA core) in the axial direction due to hydration and the peripheral mesh ring will also limit radial expansion as discussed above. The implant 10 may have certain swelling properties and may be able to expand in all directions between about 1-5% between demolding and full hydration and while unloaded. Also, the implant 10 can be configured to regain height by rehydration when unloaded after height loss due to compressive force. The device 10 may not gain height in situ if unloaded if it does not lose height in the first place.

One primary purpose of the peripheral mesh ring 12 can be to increase radial strength to limit radial expansion under load. The mesh ring 12 may be embedded in the molded material to a sufficient degree so that it does not promote or have significant tissue in-growth. In addition, the tissue in-growth is inhibited if the mesh is not exposed or if the pore size is too small. For example, an exposed peripheral mesh layer having a very small pore size may not experience in-growth.

As noted above, one primary purpose of the mesh on the endplates 11, 13 can be to promote attachment of the device's endplate to the vertebral bodies, primarily by tissue in-growth. To that end, the mesh on at least one of the endplates 11, 13 can be processed before, during and/or after molding to locally expose mesh that otherwise would be or is covered with molded material (e.g., hydrogel) in order to promote the tissue in-growth. The exposure can be carried out so that the mesh is configured to allow for double integration of mesh for fixation of orthopaedic devices: on the one hand, fixation with the device's main material (in some embodiments, hydrogel) and on the other hand, fixation with human tissues (fibrous and/or bone, depending on location and use of the implanted device).

However, the flexible keel 15 can comprise other materials and can be formed or provided in other ways. For example, as shown in FIG. 6A, the keel 15' can include two outwardly extending flexible members 18, 19 (which may be formed by two discrete end portions of mesh material bent upwardly or may be formed by a cut along the fold line). FIG. 6C illustrates that a triple fold 15f can be used to form a keel 15" and FIG. 6B illustrates a double fold 15f can be used to form a keel 15'''.

Although shown in FIGS. 1A-1C, 2A and 2B as defined by a material layer on an outer surface of the implant body, the keel 15 can be defined by a material layer molded subsurface and/or embedded a distance into the implant body and anchored therein to extend a desired distance above or below the bounds of the implant body.

In other embodiments, the implants 10 may be articulating implants with metallic or non-molded members. The flexible keel 15 can be ultrasonically welded, staked, brazed, adhesively attached, screwed, nailed or otherwise affixed, attached and/or mounted to a desired component to provide the flexible keel 15. In some-embodiments, the flexible keel 15 can be formed using non-elastomeric or non-polymer biocompatible materials including malleable metals, metallic mesh and/or non-porous materials. For non-porous materials, the macropores can be arranged to provide sufficient fixation.

In some embodiments, the shape of the implant 10 can be described as a three-dimensional structure that provides anatomical shape, shock absorbency and mechanical support. The anatomical shape can have an irregular solid volume to fill the target intervertebral disc space. The coordinates of the body can be described using the anatomic directions of superior (towards the head), inferior (towards the feet), lateral (towards the side), medial (towards the midline), posterior (towards the back), and anterior (towards the front). From a superior view, the implanted device has a kidney shape with the hilum towards the posterior direction. The margins of the device in sagittal section are generally contained within the vertebral column dimensions. The term "primary surface" refers to one of the superior or inferior surfaces.

The size of the prosthetic spinal disc 10 can vary for different individuals. A typical size of an adult lumbar disc is 3-5 cm in the minor axis, 5 cm in the major axis, and 1.5 cm in thickness, but each of these dimensions can vary. It is contemplated that the implant 10 can be provided in a range of predetermined sizes to allow a clinician to choose an appropriate size for the patient. That is, the implant 10 can be provided in at least two different sizes with substantially the same shape. In some embodiments, the implant 10 can be provided in small, medium and large sizes. Further, the sizes can be configured according to the implant position—i.e., and L3-L4 implant may have a different size from an L4-L5 implant. In some embodiments, an implant 10 can be customized (sized) for each respective patient.

The implant 10 can be configured as a flexible elastomeric MRI compatible implant of a shape generally similar to that of a spinal intervertebral disc. The implant 10 can have a solid elastomeric body with mechanical compressive and/or tensile elasticity that is typically less than about 100 MPa (and typically greater than 1 MPa), with an ultimate strength in tension generally greater than about 100 kPa, that can exhibit the flexibility to allow at least 2 degrees of rotation between the top and bottom faces with torsions greater than 0.01 N-m without failing. The implant 10 can be configured to withstand a compressive load greater than about 1 MPa.

The implant 10 can be made from any suitable elastomer capable of providing the desired shape, elasticity, biocompatibility, and strength parameters. The implant 10 can be configured with a single, uniform average durometer material and/or may have non-linear elasticity (i.e., it is not constant). The implant 10 may optionally be configured with a plurality of durometers, such as a dual durometer implant. The implant 10 can be configured to be stiffer in the middle, or stiffer on the outside perimeter. In some embodiments, the implant 10 can be configured to have a continuous stiffness change, instead of two distinct durometers. A lower durometer corresponds to a lower stiffness than the higher durometer area. For example, one region may have a compressive modulus that is between about 11-100 MPa while the other region may have a compressive modulus that is between 1-10 MPa.

The implant 10 can have a tangent modulus of elasticity that is about 1-10 MPa, typically about 3-5 MPa, and water content of between about 30-60%, typically about 50%.

Some embodiments of the implantable spinal disc 10 can comprise polyurethane, silicone, hydrogels, collagens, hyalurons, proteins and other synthetic polymers that are configured to have a desired range of elastomeric mechanical properties, such as a suitable compressive elastic stiffness and/or elastic modulus. Polymers such as silicone and polyurethane are generally known to have (compressive strength) elastic modulus values of less than 100 MPa. Hydrogels and collagens can also be made with compressive elasticity values less than 20 MPa and greater than 1.0 MPa. Silicone, polyurethane and some cryogels typically have ultimate tensile strength greater than 100 or 200 kiloPascals. Materials of this type can typically withstand torsions greater than 0.01 N-m without failing.

As shown in FIG. 1, the spinal disc body 10 may have an circumferential surface 12, a superior surface 11, and an inferior surface 13. The superior and inferior surfaces 11, 13 may be substantially convex to mate with concave vertebral bones or may be planar or even concave (and one surface may have a different configuration than the other). The circumferential surface 12 of spinal disc body 10 corresponds to the annulus fibrosis ("annulus") of the natural disc and can be described as the annulus surface 12. The superior surface 11 and the inferior surface 13 of spinal disc body 10 correspond to vertebral end plates ("end plates") in the natural disc. The medial interior of spinal disc body 10 corresponds to the nucleus pulposus ("nucleus") of the natural disc.

The implant 10 can include a porous covering, typically a mesh material layer, 11c, 13c on each of the superior and inferior primary surfaces 11, 13, respectively. As shown, the implant 10 can also include a porous, typically mesh, material layer 12c on the annulus surface 12. The annulus cover layer 12c can be formed as a continuous or seamed ring to inhibit lateral expansion. In other embodiments, the annulus cover layer 12c can be discontinuous. As also shown, the three coverings 11c, 12c, 13c can meet at respective edges thereof to encase the implant body 10. In other embodiments, the coverings 11c, 12c, 13c may not meet or may cover only a portion of their respective surfaces 11, 12, 13.

FIG. 1B illustrates that the annulus cover 12c and the superior cover 11c can be oversized to extend beyond the bounds of the implant body and meet at a curvilinear upper anterior portion 20 of the implant 10. Bone screws 50 or other attachment mechanisms can extend through these curvilinear segments 20 to help hold the implant in position in the patient's body. Similarly, the inferior cover 13c can meet the annulus cover 12c at a curvilinear lower anterior portion 21 of the implant. As shown in FIG. 1C, this configuration of the cover 11c allows the use of four bone screws 50. Additional or alternate attachment means, such as additional curved segments, or alternative attachment means can be employed such as a skirt 14 (FIG. 2A) integral tabs and the like, to allow for bone attachment configurations. Each curved segment or other configuration of tabs 21 can have a height between about a 2 mm-15 mm with a length (side-side width) being typically about 10 mm. The tabs 21 are located around the periphery of the implant (the tabs are disposed about the top and bottom). The tabs 21 can be provided by a single continuous skirt, or provided as discrete tab segments.

Alternatively, the annulus cover 12c may terminate adjacent or inside the bounds of the annulus surface, or the superior or inferior covers 11c, 13c may terminate adjacent or within the bounds of the respective superior or inferior surfaces and not extend beyond the bounds of the implant. In such an embodiment, an outer portion of the superior or inferior covers 11c, 13c alone, or an upper or lower portion of the annulus cover 12c alone, can be used to receive and attach the bone screw(s) and/or other attachment mechanisms 50. The coverings may connect continuously or intermittently about respective perimeters, or may be spaced apart and not meet at all.

Figure 2A:
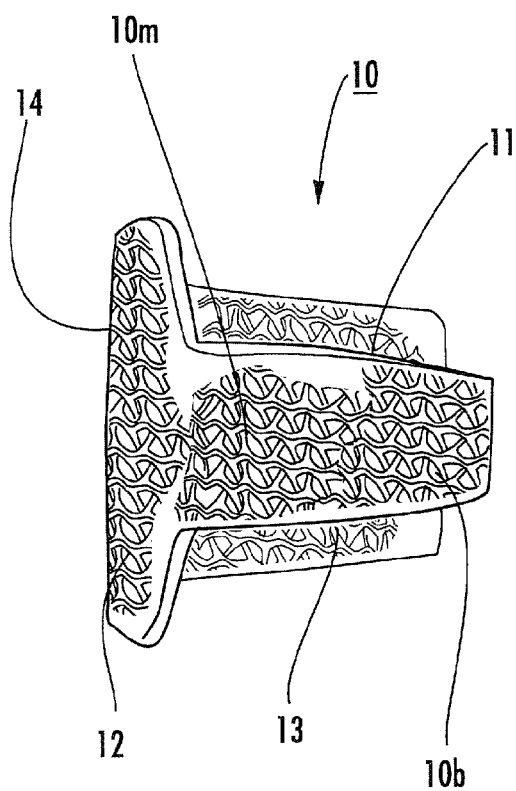
FIG. 2A is a side view of an implantable spinal disc prosthesis with a keel and skirt according to embodiments of the invention.
Figure 2B:
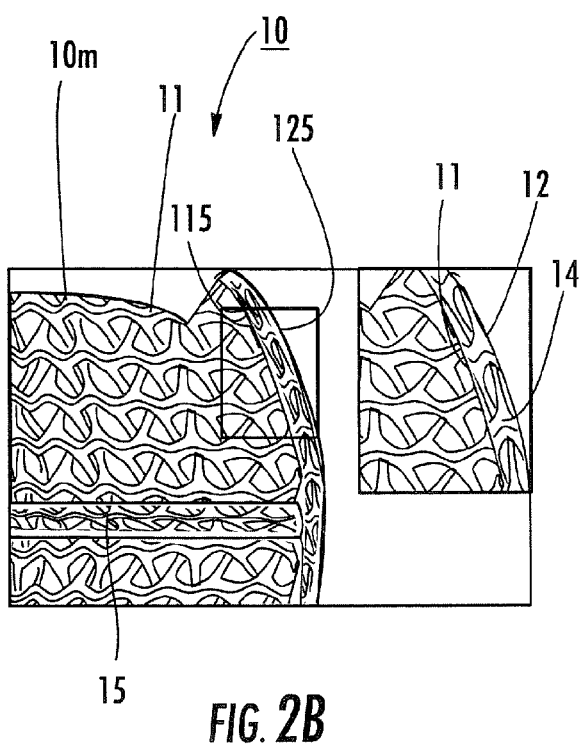
FIG. 2B is a partial enlarged top view of the device shown in FIG. 2A.

As shown in FIGS. 1A and 2A, the implant 10 can be configured to be substantially encased in the same porous, typically mesh, material covering in the same thickness as that which forms the keel 15. Alternatively, different material layers or different thickness of material layers can be used on different surfaces. For example, the annulus material layer 12c may have additional thickness relative to the covering layer 11c, 13c on the superior or inferior surfaces 11, 13 of the implant.

Although shown as substantially conformally covering substantially the entire respective surfaces, the covers 11c, 12c, 13c may occupy a smaller portion of the respective surface 11, 12, 13, such as a minor portion (not shown). The coverings 11c, 12c, 13c can be configured to allow substantially vertical passive expansion or growth of between about 1-40%, typically, about 20-30%, in situ as the implant 10 absorbs or intakes liquid due to the presence of body fluids. The passive growth can be measured outside the body by placing an implant in saline at room temperature and pressure for 5-7 days, while held in a simulated spinal column in an invertebrate space between two simulated vertebrates. It is noted that the passive expansion can vary depending, for example, on the type of covering or mesh employed and the implant material. For example, in some embodiments, the mesh coverings 11c, 12c, 13c along with a weight percentage of (PVA) used to form the implant body are configured to have between about 1-5% expansion in situ.

In the embodiment shown in FIGS. 1A-1C, the keel 15 has a fold or loop 15f formed such that the tip of the fold 15t is closed and the two legs $15_1$, $15_2$ are spaced apart to define an elongate gap space 15g (FIG. 1B) therebetween. FIG. 8 illustrates that the spacing can be such that the keel 15 has a tent-like cross-sectional or end view shape with a top angled (rather than rounded) corner. FIG. 1A illustrates that the spacing can be such that the keel legs $15_1$, $15_2$ are in contact via their inner surfaces over a major portion of its length.

In end view, such as shown in FIG. 1C, the keel 15 can include a closed tip or crown 15t and closely spaced legs of the folds $15_1$, $15_2$. The legs $15_1$, $15_2$ can merge into the conformal covering material 12c, 13c. The legs $15_1$, $15_2$ can contact as they approach the implant body 10 or can be spaced apart a distance such as about 0.01 mm to about 10 mm, typically between about 0.1 mm to about 1 mm.

In some embodiments, the legs $15_1$, $15_2$ may be attached (continuously or discontinuously) along a lengthwise direction at one or more of an upper, medial or lower portion, or may have other structural reinforcement means (not shown). Portions of the keel 15 can be attached via any suitable biocompatible attachment means, such as heat-sealed, ultrasonically attached, molded, adhesively bonded or stitched together. Alternatively, or additionally, the legs of the fold $15_1$, $15_2$ may have horizontal, vertical or angled stiffeners or other reinforcement means.

In addition, in some embodiments, the keel 15 may comprise a biocompatible coating or additional material on an outer and/or inner surface and/or in the gap space that can increase the stiffness of the keel 15. See also, FIGS. 5A-5C. The stiffening coating or material can include PVA cryogel applied as a liquid or applied as a discrete insert before or during the molding process. The annulus cover 11C (also described as a "skirt") may also include stiffening or reinforcement means such as those described herein for the keel 15.

As shown in FIG. 7A, the keel 15 can include a plurality of spaced apart apertures 40. The apertures 40 can be macropores formed through the wall(s) of the keel 15 that can facilitate bone and/or tissue in-growth. The apertures 40 can be aligned or misaligned over at least a major portion of a length of the keel 15. The one or more apertures can be formed as pre-molding apertures and/or post-molding apertures 40 in the keel 15 and/or skirt 14 for vertebral bone attachment. If a cutting process is used, the cutting process (e.g., ultrasonic cutting, laser cutting, thermal cutting, RF cutting or other suitable techniques) may locally melt the two layers of mesh (endplate mesh and skirt mesh) or keel pieces together, creating at that point a fused direct connection between the two pieces or layers. In some embodiments, the apertures 40 or through-holes can be created into the flexible keel 15 by cutting/removing the material (hydrogel+mesh) using a die or a punch, or by separating/spreading the material around the hole to be created using a puncturing, cutting and/or penetrating device such as a needle or equivalent that can be inserted through a keel wall at a desired position(s). The needle or other suitable device can be maintained in the material through the thermal cycling of the implant (curing), which allows the aperture 40 to remain at a similar dimension after removal of the needle or other suitable aperture forming device.

In some embodiments, alternatively or additionally, as shown for example in FIG. 7B, the mesh defining the flexible keel 15 can be locally exposed 15e to allow for tissue ingrowth, such as by washing away the hydrogel material or by selectively molding regions of the mesh to provide at least partially exposed surfaces to a partial or full depth of the mesh that can promote tissue ingrowth. The locally exposed portions of the mesh will be thinner 15t relative to the hydrogel-embedded mesh regions 15i. The non-exposed portions of the mesh may be embedded with the molded material on each side of the mesh (the molded material can add extra thickness to each side of the mesh layer) thereby providing increased thickness and rigidity as shown in FIG. 7B. See, e.g. co-pending, co-assigned, U.S. Provisional Application Ser. No. 60/885,682, for additional description of exemplary localized mesh exposure systems and methods, the contents of which are hereby incorporated by reference as if recited in full herein.

FIG. 10A illustrates that one or more keels 15 can occupy or span a subportion (less than the entire distance) of the respective primary surface. As shown in FIG. 10A, the superior surface 12 can include two spaced apart axially aligned keels 15a. The keels 15a can have the configurations discussed elsewhere. In the embodiment shown, the keels 15a have different shapes as they extend from the same surface and can have different configurations as they extend from different primary surfaces (i.e., the respective inferior and superior surfaces). FIG. 10B illustrates that the keels 15a can include macropores or other apertures 40.

Figure 11A:
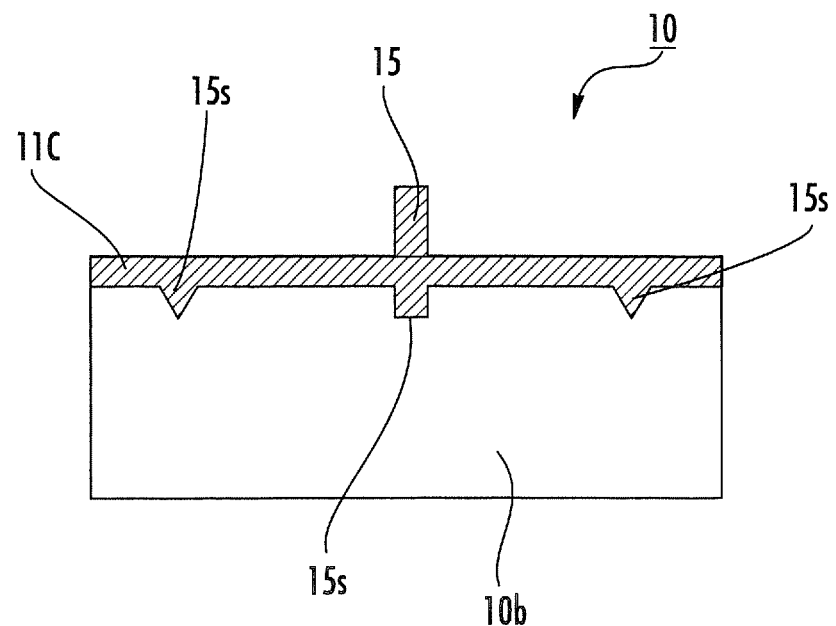
FIGS. 11A and 11B are cross-sectional schematic illustrations of implants with keels and subsurface attachment segments according to embodiments of the present invention.
Figure 11B:
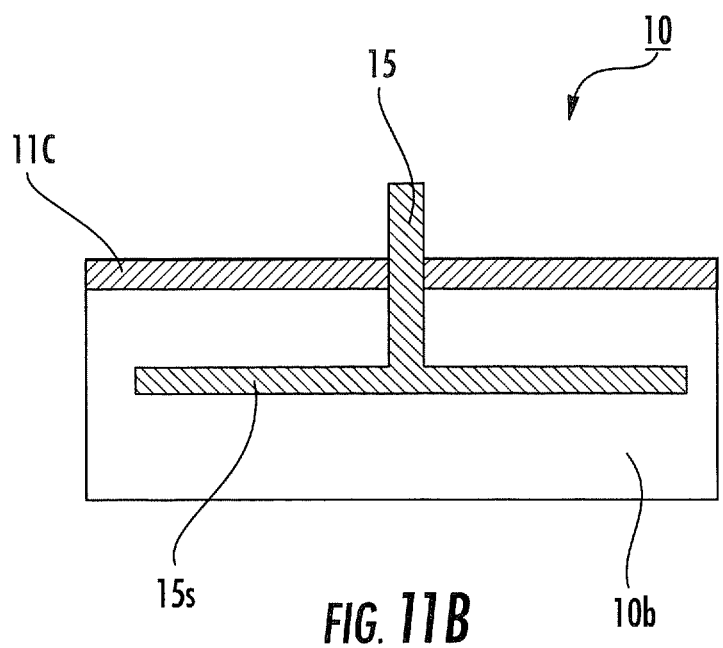

FIGS. 11A and 11B illustrate that the keel 15 can be configured with subsurface attachment segments 15s. As shown in FIG. 11A, the implant 10 has a primary body 10b (typically a molded elastomeric body) and the keel 15 has subsurface attachment segments 15s that extend a minor distance into the implant body 10b (such as, for example, between about 5-30% of the cross-sectional distance). As shown in FIG. 11A, an outer (mesh) layer 11c may reside on the outside of the implant body 10b with the subsurface attachment segments 15s disposed thereunder. The segments 15s can be integrally attached to the liner layer 11c prior to securing to the primary implant body 10b or may be attached during the fabrication process. FIG. 11B illustrates that the flexible keel 15 can be defined by anchoring a layer thereof into the implant body 10b. An optional outer liner 11c may be placed about the keel 15. Different materials can be used to form the keel 15 and subsurface segments 15s and the liner 11c, where used. Also, although shown as extending from one primary surface for discussion, the implant 10 can be configured with one or more keels 15 that extend from the other or both surfaces (and this is applicable to other embodiments shown or discussed herein).

Some embodiments of the spinal disc implant 10 are configured so that they can mechanically function as a substantially normal (natural) spinal disc and can attach to endplates of the adjacent vertebral bodies. The implant 10 can expand in situ to restore the normal height of the intervertebral space. The implant 10 can be configured to expand, for example, between about 1-40%, typically about 20%, after implantation relative to its configuration at the time of implantation. It is envisioned that the spinal disc implant 10 can be inserted by a surgical procedure into the target intervertebral space. It may be used for separation of two bony surfaces within the spine. In other embodiments, the implant may be configured for use with respect to other bones of the body.

As shown, for example, in FIGS. 4A, 4B and 6A-C, the spinal disc implant 10 can be substantially rectangular when viewed from at least one side. As shown in FIGS. 1A and 2A, the superior surface 11 and the interior surface 13 can be shaped to be substantially convex in order to provide a good interface with the superior and inferior vertebral bodies, 16 and 17 (FIGS. 1B, 1C), respectively.

As shown in FIG. 1A, the spinal disc body 10 is generally of kidney shape when observed from the superior, or top, view, having an extended oval surface and an indented portion. As shown in FIG. 1B, the anterior portion 10a of spinal disc 10 can have greater height than the posterior portion 10p of spinal disc 10 in the sagittal plane. The implant 10 can be configured with a mechanical compressive modulus of elasticity of about 1.0 MPa, ultimate stretch of greater than 15%, and ultimate strength of about 5 MPa. The device can support over 1200 N of force. Further description of an exemplary flexible implant is described in co-pending U.S. Patent Application Publication No. 20050055099, the contents of which are hereby incorporated by reference as if recited in full herein.

Elastomers useful in the practice of the invention include silicone rubber, polyurethane, polyvinyl alcohol (PVA) hydrogels, polyvinyl pyrrolidone, poly HEMA, HYPAN™ and Salubria® biomaterial. Methods for preparation of these polymers and copolymers are well known to the art. Examples of known processes for fabricating elastomeric cryogel material is described in U.S. Pat. Nos. 5,981,826 and 6,231,605, the contents of which are hereby incorporated by reference. See also, Peppas, Poly(vinyl alcohol) hydrogels prepared by freezing-thawing cyclic processing. Polymer, v. 33, pp. 3932-3936 (1992); Shauna R. Stauffer and Nikolaos A. Peppas.

Figure 12:
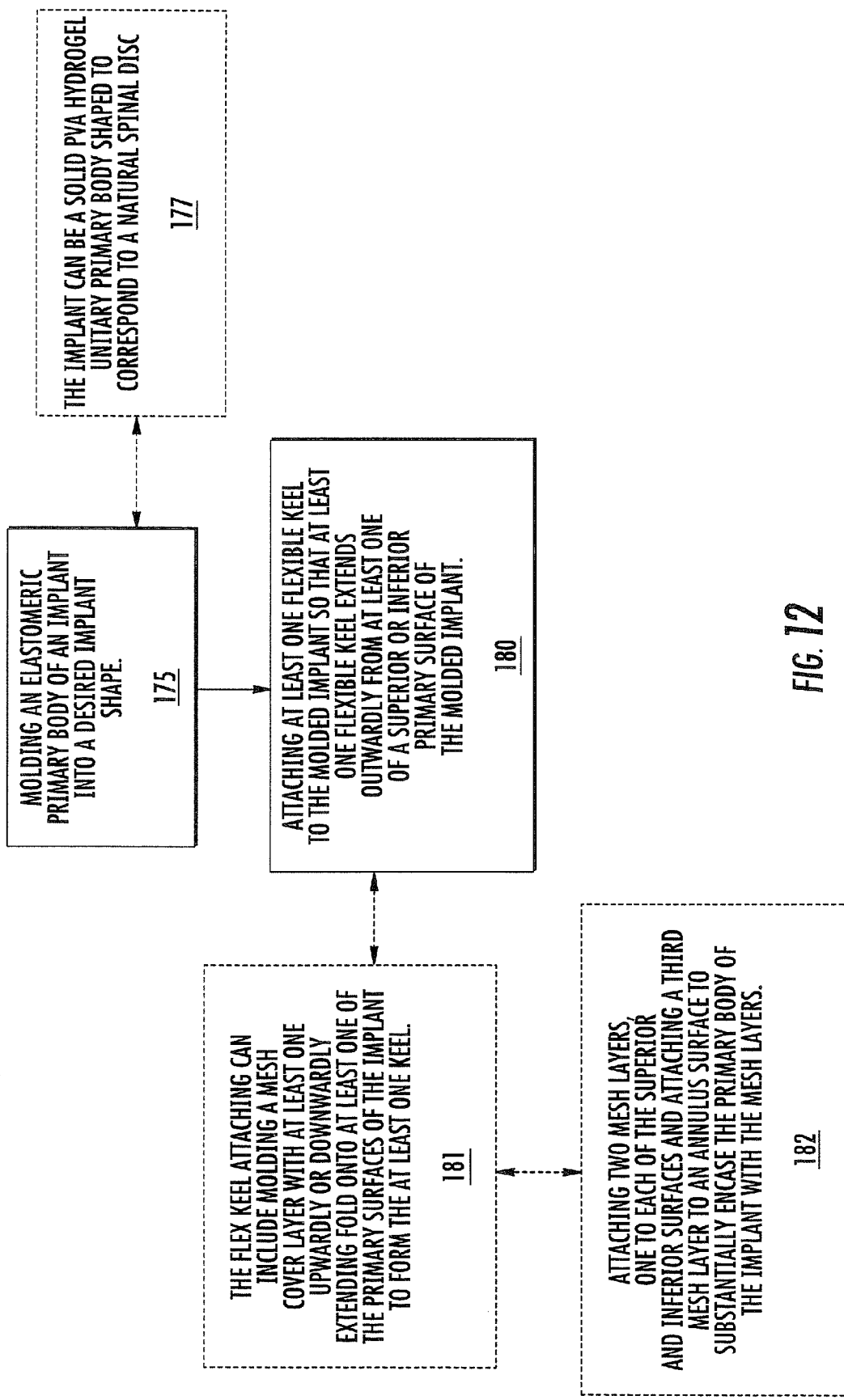
FIG. 12 is a flow chart of operations that can be used to fabricate a flexible keel spinal disc implant according to embodiments of the present invention.

FIG. 12 is a flow chart of exemplary operations that can be carried out to form an implant with at least one flexible keel according to embodiments of the present invention. Although described herein as particularly suitable for spinal disc implants, it is contemplated that the methods of fabricating implants and/or keels can be used for other implants as well. An elastomeric primary body of an implant can be molded into a desired implant shape (block 175). At least one flexible keel can be attached to the molded implant so that the at least one flexible keel extends outwardly form at least one of a superior or inferior surface of the molded implant (block 180).

In some embodiments, the implant is a solid PVA hydrogel having a unitary body shaped to correspond to a natural spinal disc (block 177). An exemplary hydrogel suitable for forming a spinal implant is (highly) hydrolyzed crystalline poly(vinyl alcohol) (PVA). PVA cryogels may be prepared from commercially available PVA material, typically comprising powder, crystals or pellets, by any suitable methods known to those of skill in the art. Other materials may also be used, depending, for example, on the application and desired functionality. Additional reinforcing materials or coverings, radiopaque markers, calcium sulfates or other materials or components can be molded on and/or into the molded body. The keel 15 may incorporate one or more radiopaque marker to allow confirmation of position during surgery and throughout follow-up of patient. The marker may be a radiopaque wire (titanium, tantalum . . . ) located internally at the rim/fold of the keel and/or woven into the mesh. It also comprise a radiopaque ink printed on the inner and/or outer mesh surfaces. Alternatively, the implant can consist essentially of only the molded PVA body.

In some embodiments, the flex keel can be attached by molding a mesh cover layer with at least one upwardly or downwardly extending fold onto at least one of the primary surfaces (block 181). Optionally, two mesh layers can be attached to the implant body, one to each respective superior and inferior surface and a third mesh layer can be attached to the annulus surface to substantially encase the implant body (block 182).

Figure 13A:
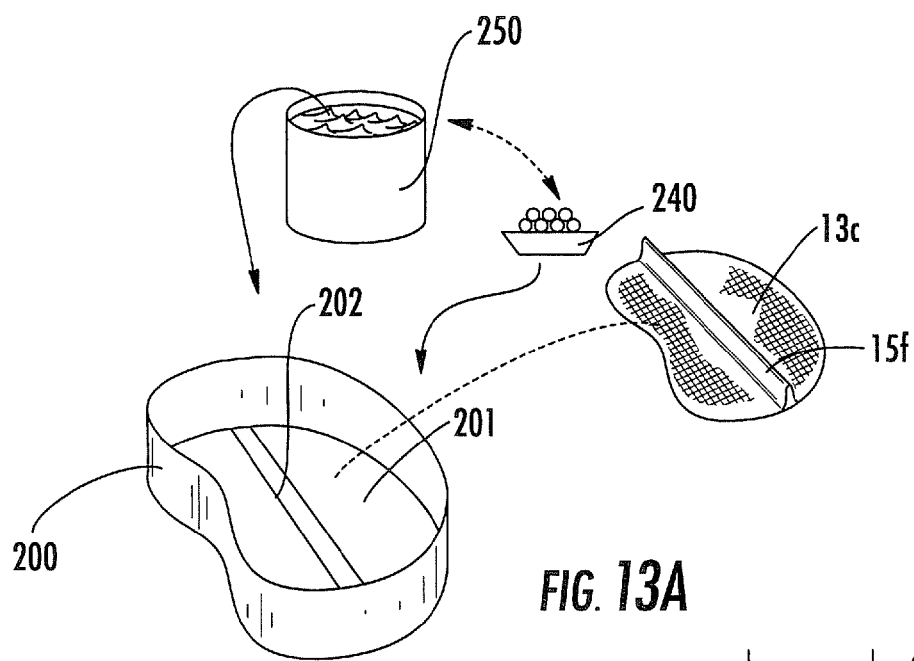
FIG. 13A is a schematic illustration of a spinal disc implant mold configured to receive moldable implant material to form a spinal disc implant according to embodiments of the present invention.

Referring to FIG. 13A, in some embodiments, a moldable material is placed in a mold 200. The moldable material comprises an irrigant and/or solvent 250 and about 25 to 60% (by weight) PVA powder crystals 240. The PVA powder crystals can have a MW of between about 124,000 to about 165,000, with about a 99.3-100% hydrolysis. The irrigant or solvent 250 can be a solution of about 0.9% sodium chloride. The PVA crystals 240 can be placed in the mold 200 before the irrigant (no pre-mixing is required). The mold 200 has the desired 3-D implant body shape. As shown, the mold 200 includes a floor 201 with a channel or aperture 202 that is sized and configured to receive the keel 15 of a respective cover layer 13c (shown as layer 13c, but the floor 201 could receive layer 12c, depending on the mold orientation).

Figure 13B:
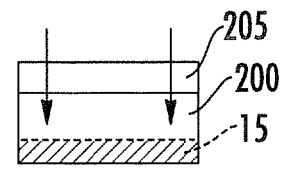
FIG. 13B is a schematic illustration of the mold shown in FIG. 13A with a lid thereon.

As shown in FIG. 13B, a lid 205 can be used to close the mold 200. The closed mold 200 can be evacuated or otherwise processed to remove air bubbles from the interior cavity. For example, the irrigant can be overfilled such that when the lid is placed on (clamped or secured to) the mold 200, the excess liquid is forced out thereby removing air bubbles. In other embodiments, a vacuum can be in fluid communication with the mold cavity to lower the pressure in the chamber and remove the air bubbles. The PVA crystals and irrigant can be mixed once in the mold before and/or after the lid is closed. Alternatively, the mixing can occur naturally without active mechanical action during the heating process. In some embodiments, a hydrogel insert 15m (FIG. 5A) can be placed in the keel 15 or the mesh can be folded about the insert before the molding process. The mesh/insert sub-assembly is then used in the casting process as described. The use of a hydrogel insert can ensure a proper filling of the keel cavity with hydrogel in order to embed the mesh material forming the keel.

As also shown in FIG. 13B, the keel 15 can reside in the floor channel or aperture 202 below the floor 201. The lid 205 can be similarly configured where keels are desired on both primary surfaces. The irrigant 250 and PVA crystals 240 in the mold 200 are heated. Typically, the mold with the moldable material is heated to a temperature of between about 80° C. to about 200° C. for a time sufficient to form a solid molded body. The temperature of the mold can be measured on an external surface. The mold can be heated to at least about 80-200° C. for at least about 5 minutes and less than about 8 hours, typically between about 10 minutes to about 4 hours, the (average or max and min) temperature can be measured in several external mold locations. The mold can also be placed in an oven and held in the oven for a desired time at a temperature sufficient to bring the mold and the moldable material to suitable temperatures. In some embodiments, the mold(s) can be held in an oven at about 100-200° C. for about 2-6 hours, the higher range may be used when several molds are placed therein, but different times and temperatures may be used depending on the heat source, such as the oven, the oven temperature, the configuration of the mold, and the number of items being heated.

Figure 14A:
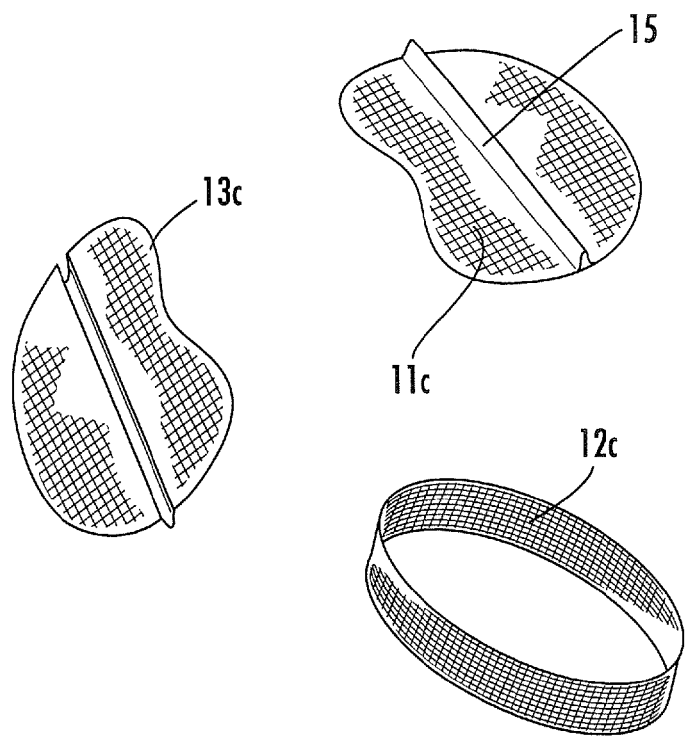
FIG. 14A is a schematic illustration of a three-piece outer covering that can be integrally attached to a molded elastomeric body according to embodiments of the present invention.

FIG. 14A illustrates that one or more of the three covering layers 11c, 12c, 13c can be placed in the mold as pre-cut or shaped components before the PVA crystals and/or irrigant. The liners 11c, 12c, 13c integrally attach to the molded implant body during the molding process. In some embodiments, osteoconductive material, such as, for example, calcium salt can be placed on the inner or outer surfaces of the covering layers 11c, 12c, 13c, and/or the inner mold surfaces (wall, ceiling, floor) to coat and/or impregnate the mesh material to provide osteoconductive, tissue-growth promoting coatings.

Figure 14B:
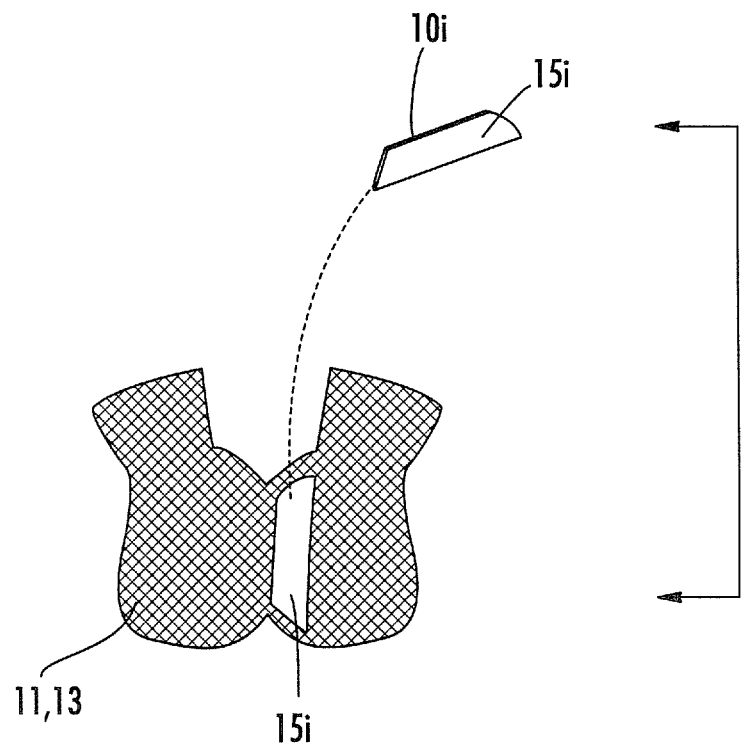
FIG. 14B is an exploded view of a moldable keel insert that can be assembled to a mesh layer with a keel segment prior to molding according to embodiments of the present invention.
Figure 14C:
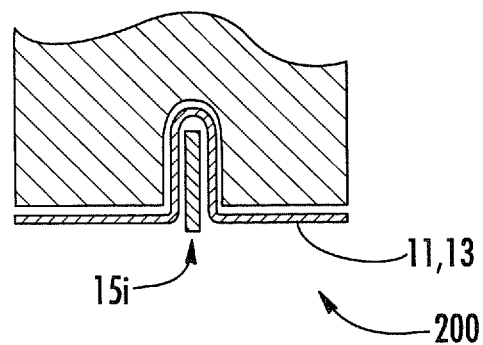
FIG. 14C is a partial side section view of the insert and keel shown in FIG. 14B in a mold core prior to molding according to embodiments of the invention.
Figure 14D:
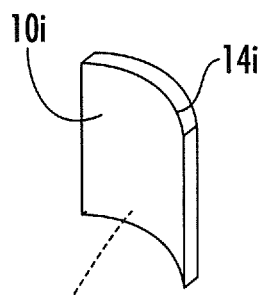
FIG. 14D is a side perspective view of a skirt insert according to embodiments of the present invention.
Figure 14E:
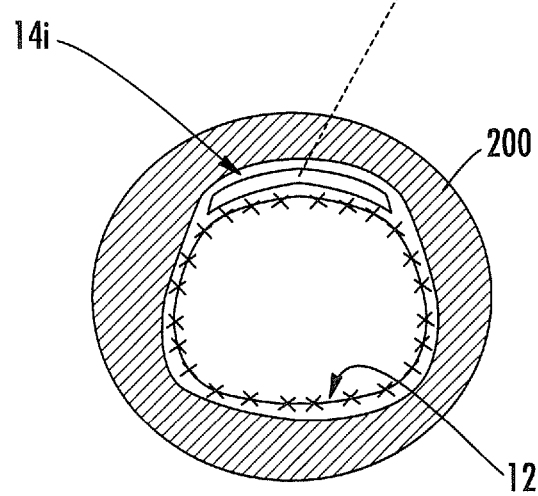
FIG. 14E is a top section view of a mold with the skirt insert of FIG. 14D placed between a skirt portion of an annular ring and the inner wall of a mold cavity according to embodiments of the present invention.

The mold 200, 201 and members 11c, 12c, 13c can be configured to provide the bone attachment extension segments 20, 21, discussed above. FIGS. 14A-14E illustrate that pre-formed inserts of material 10i, such as, for example, hydrogel, can be placed selectively in the mold 200 to facilitate suitable mold material penetration into the mesh substrate 10m during molding/casting. As shown in FIGS. 14A and 14B, the insert 10i is a keel insert 15i that can be placed inside a keel fold region of the superior and/or inferior endplate mesh 11, 13, respectively, then the mesh 11, 13 with the insert 15i can be placed in the superior and/or inferior mold core region of the mold 200. FIGS. 14C and 14D illustrate another insert 10i, shown as a skirt insert 14i, can be placed between the skirt segment 14 of the annular mesh 12, and the inner wall of the mold cavity 200.

After heating, the implant body can be cooled passively or actively and/or frozen and thawed a plurality of times until a solid crystalline implant is formed with the desired mechanical properties. The molded implant body can be removed from the mold prior to the freezing and thawing or the freezing and thawing can be carried out with the implant in the mold. Alternatively, some of the freeze and thaw steps (such as, but not limited to, between about 0-10 cycles) can be carried out while the implant is in the mold, then others (such as, but not limited to, between about 5-20 cycles) can be carried out with the implant out of the mold.

Before, during and/or after freezing and thawing (but typically after demolding), the molded implant 10 can be placed in water or saline (or both or, in some embodiments, neither). The device 10 can be partially or completely dehydrated for implantation. The resulting prosthesis can have an elastic modulus of at least about 2 MPa and a mechanical ultimate strength in tension and compression of at least 1 MPa, preferably about 10 MPa, and under about 100 MPa. The prosthesis may allow for between about 1-10 degrees of rotation between the top and bottom faces with torsions of at least about 1 N-m without failing. The implant can be a single solid elastomeric material that is biocompatible by cytotoxicity and sensitivity testing specified by ISO (ISO 10993-5 1999: Biological evaluation of medical devices—Part 5: Tests for in vitro cytotoxicity and ISO 10993-10 2002: Biological Evaluation of medical devices—Part 10: Tests for irritation and delayed-type hypersensitivity.).

The testing parameters used to evaluate the compressive tangential modulus of a material specimen can include:

| | |
|---|---|
| Test type: | unconfined compression |
| Fixtures: | flat platens, at least 30 mm diameter |
| Rate: | 25.4 mm/sec to 40% strain |
| Temperature: | room temp (~22° C.) |
| Bath: | samples stored in saline or water until immediately before test |
| Samples: | cylinders, 9.8 ± 0.1 mm height, 9.05 ± 0.03 mm diameter |

Compressive Tangential Modulus calculated at 15, 20, and 35% strain

FIG. 15 is a schematic illustration of an exemplary production system 500 that can be used to fabricate spinal implants according to embodiments of the present invention. As shown, a series of mold shells 225 holding a plurality of molds 200 can be serially advanced along a process line. The mold shells 225 can be advanced via a belt drive or conveyor system 510. At a first station A (515), the desired liner 11c, 13c can be placed in the molds 200. Where flexible keels 15 are formed on the implant using the liner material (12c or 13c), the mold floor 201 can include a receiving channel or aperture 202 (FIGS. 16A-16C).

At a next station B (518), the mold material 245 can be added to the molds 200. As shown, the mold material includes PVA 240 that is added first, then liquid 250 that is added next. However, it is noted that, in other embodiments, the mold material can be added as a flowable liquid (the PVA and liquid or other elastomeric constituents can be pre-mixed and may be pre-heated to form a viscous flowable slurry or mixture). The mold shells 225 can optionally vibrate or oscillate to mix the mold material as the mold shells move along the process flow path.

At station C (520), a top layer 12c can be placed on the material in the mold 200. A lid 205 can be used to close the mold 200. In embodiments wherein a flexible keel 15 is formed using the top layer 12c, a ceiling in the lid 205c can include a keel receiving aperture or channel 206, similar to the floor aperture or channel 202 discussed herein. The closed mold can be advanced to station D (522) where the molds 200 are exposed to a heat source 299 and heated to a desired time and temperature sufficient to impart the desired heat for a desired time to the moldable material held in the molds 200. The heat source 299 can be a stationary oven and the molds 200 can be placed on columns of racks therein. Alternatively, the drive system can be configured to automatically advance the molds therein and hold the molds in the oven for the desired time. Temperature sensors can be placed on and/or in the mold to confirm desired threshold temperatures are achieved for a desired time.

The implants 10 can be processed in several freeze-thaw cycles as discussed above. The implants 10 can be sterilized with sterile heated liquid or with radiation or other sterilization methods, typically after packaging in medical pouch or other suitable container to provide a sterile medical product.

FIG. 16A illustrates a mold 200 with a mold bottom 200b that holds the mold floor 201. As shown, the cover 13c includes the keel 15 that resides in the channel 202ch (FIG. 16B) or aperture 202a (FIG. 16C) in the floor 201. As also shown, the cover 11c is placed in the mold 200 adjacent the sidewall(s) 203 of the mold. In other embodiments, the keel 15 may be folded under the bottom of the covering 13c during the molding process and the floor can be configured to accommodate this region of extra thickness. The ceiling of the mold can be similarly configured.

Figure 17A:
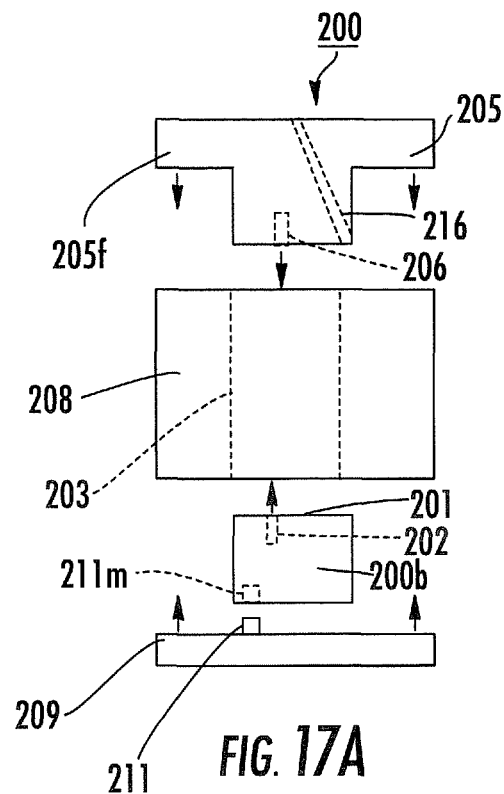
FIGS. 17A and 17B are schematic front views of a multi-component mold according to embodiments of the present invention.

FIG. 17A illustrates a multi-piece mold 200 that can be used to form implants according to embodiments of the present invention. As shown, the mold 200 includes a middle body 208, a bottom member 201 with the floor 202, a top member 205 with a ceiling 206, and a lower plate 209. The top member 205 and bottom member 201 are configured to enter opposing end portions of the middle body 208. Alignment pins 211 or other devices can be received in matable apertures 211m to help guide and/or secure the components together. The top member 205 may include a liquid and/or air vent 216. The vent 216 can allow excess irrigant (such as saline) to be expelled from the mold cavity when the lid is attached thereto. The vent 216 can be used for degassing of the mold cavity (vacuumed) before the heating step. That is, the substantially closed mold can be placed in a vacuum chamber (typically at 20-30 in Hg) for a short time, such as less than five minutes. Then the vent 216 can be closed to seal the mold before putting the sealed mold in the oven or exposing to heat using another heat source.

Figure 17B:
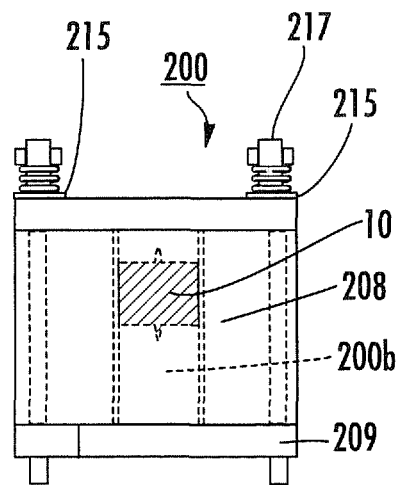
Figure 17C:
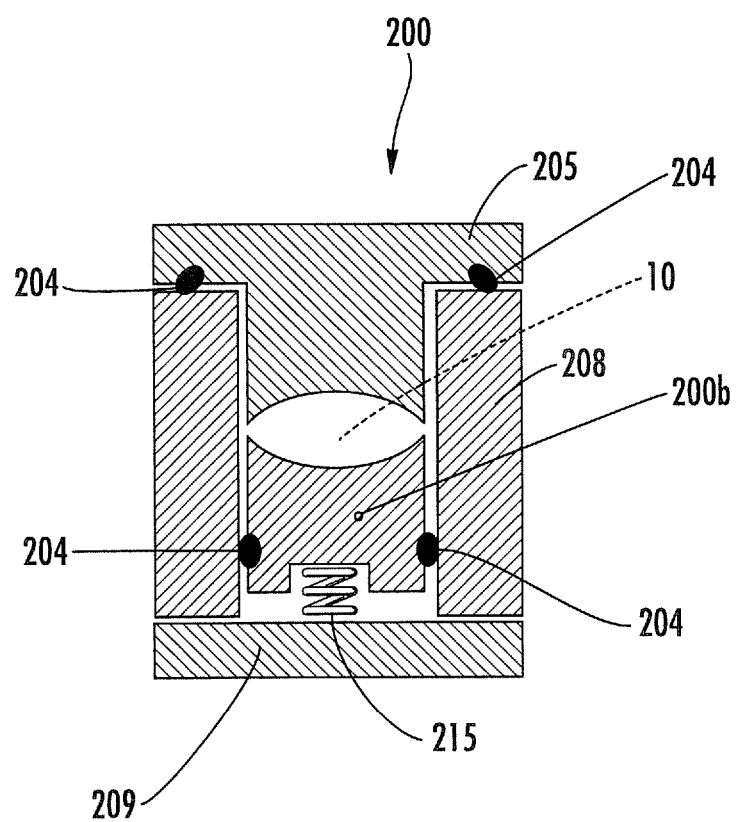
FIG. 17C is schematic section side view of a mold with a sealed floating cavity according to embodiments of the invention.

As shown in FIG. 17B, when attached, the top member 205, bottom member 201 and middle body 208 define the shape of the implant 10. The bottom member has an interior cavity that defines the floor 202 that forms the shape of the anterior portion of the implant (and, as appropriate, the aperture or channel for the keel). Similarly, the top member 205 forms the ceiling that defines the shape of the top (superior surface) of the implant. The middle body 208 defines the shape of the longitudinal (annular) perimeter of the implant. As shown, the top member 205 can include a lateral flange 205*f* that can be clamped or otherwise secured to the plate 209 to hold the mold 200 tightly together. In some embodiments, as shown, resilient members such as springs 215 (leaf springs or disc springs) can be inserted underneath one or more screw heads 217 used to attach the lid 205 to the mold body. As shown in FIG. 17C, one or more springs 215 may also or alternatively be inserted at the floor end 209. Gaskets and/or O-rings 204 can be used to maintain the seal for the mold cavity and still allow volume reduction until demolding. The springs 215 can allow limited or controlled expansion of the mold cavity while keeping the mold closed (retaining the cavity under pressure) to compensate for volume changes as the mold and the molded material therein cool down (the thermal coefficient of the mold and the molded material is typically different). Other thermal compensation mechanisms and configurations may also be used.

Figure 18:
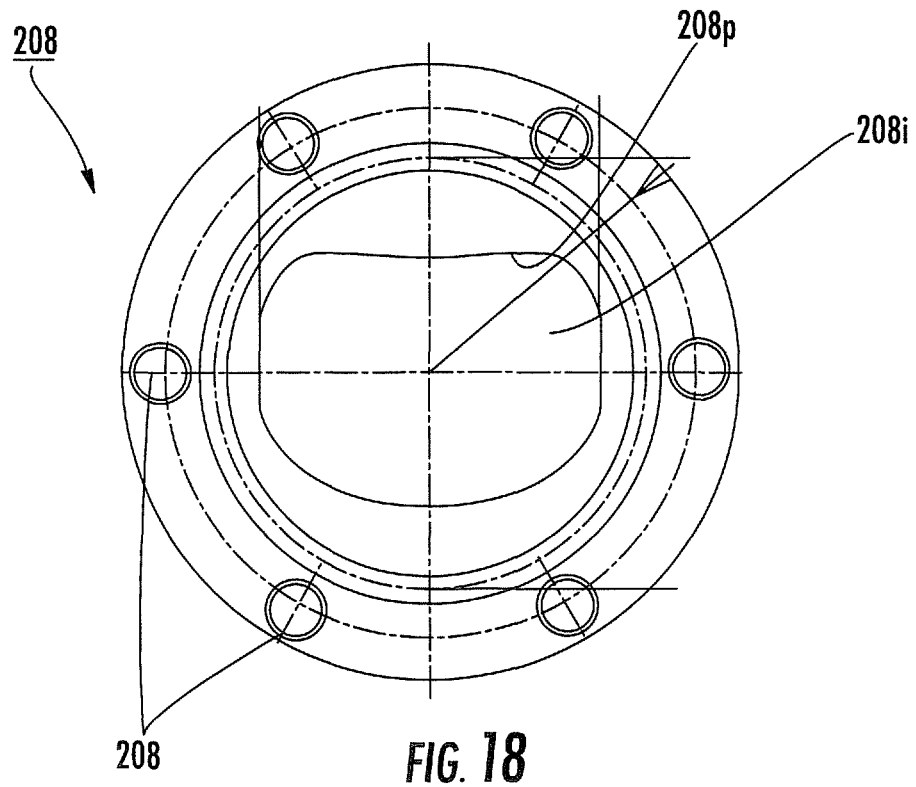
FIG. 18 is an end view of a middle body of a mold according to embodiments of the present invention.
Figure 19:
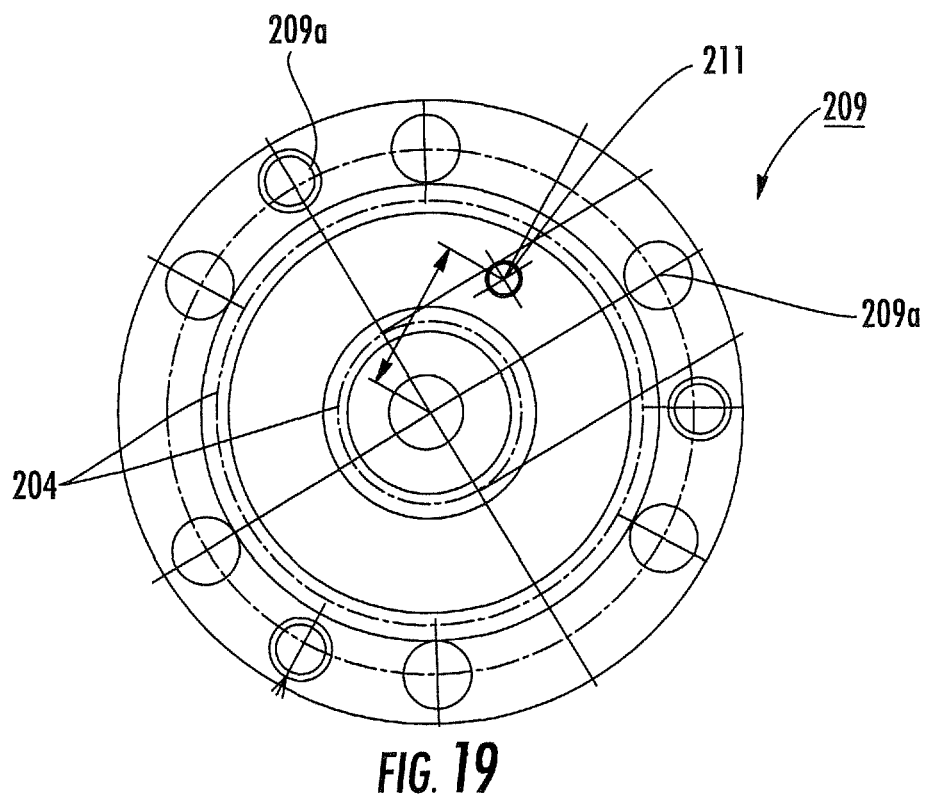
FIG. 19 is an end view of a lower plate that is attachable to the middle body shown in FIG. 18 according to embodiments of the present invention.

FIG. 18 is an end view of the middle body 208 illustrating an exemplary interior shape 208*i* that may be particularly suitable for a TDR spinal implant. As shown, the sidewall of the middle body 208 defines a perimeter wall shape of the implant 10. The middle body 208 can include circumferentially spaced apart apertures 208*a* that can align with apertures in the other matable mold components. It is noted that although the exterior of the mold 200 is shown as substantially tubular, other shapes may also be used. FIG. 19 illustrates an end view of the bottom plate 209 that can securely attach to middle body 208. The plate 209 includes apertures 209*a* as well as the guide pin 211 that is received into the bottom member 200*b* (FIG. 17A).

Figure 20A:
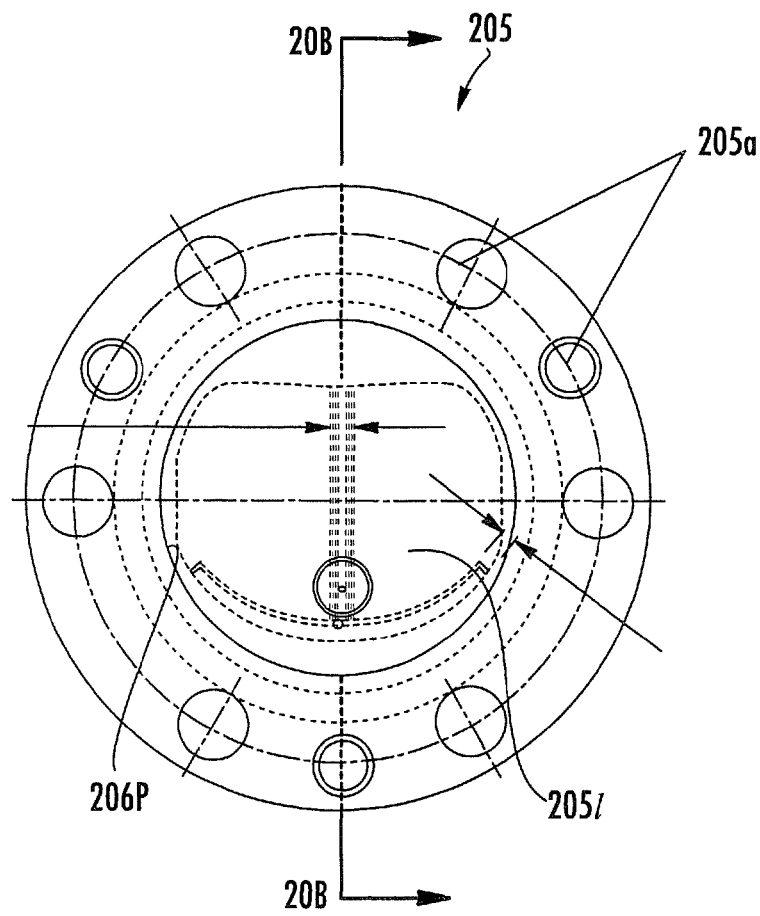
FIG. 20A is a top view of a top mold member that is attachable to the middle body shown in FIG. 18 according to embodiments of the present invention.
Figure 20B:
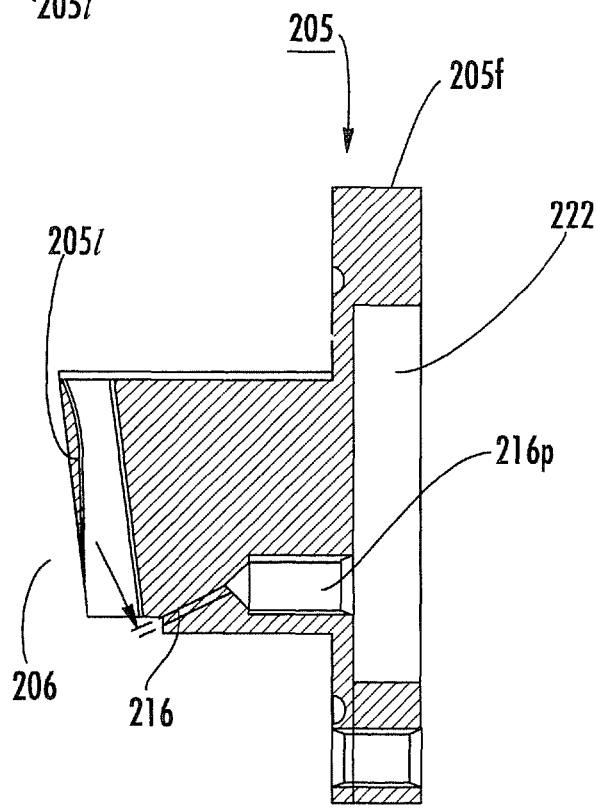
FIG. 20B is a cross-sectional view of the top mold member shown in FIG. 20A taken along line 20B-20B.

FIGS. 20A and 20B illustrate an exemplary top mold member 205. The top mold member 205 can include apertures 205*a*. As shown, the top member 205 and plate 209 can include the same number of apertures while the middle body 208 may include a lesser number. The extra holes/apertures can be used for demolding purposes (e.g., shedding or separating the mold from the molded implant). The top mold member 205 can have a lower portion that enters the middle body 208 with substantially the same perimeter shape 206*p* as the middle body perimeter shape 208*p*. The lowermost portion 205*l* of the top member 205 is shaped to define a desired moldable (superior) shape in the implant 10. As noted above, the vent 216 can be used for one or more of insertion of saline, venting of excess saline and/or degassing of the mold cavity (during evacuation with the mold in a vacuum chamber) before the heating cycle. In operation, after the lid is placed on the mold cavity, saline can be placed in the reservoir 222. The mold 200 can be placed in a vacuum chamber for a desired time. The saline is drawn into the mold cavity and air is removed via vent 216. Typically, a small amount of saline, such as less than about 10% of the volume of the reservoir, resides in the reservoir 222 after the evacuation process. The mold 200 can be sealed by attaching a screw or plug in the vent port 216*p*, shown disposed at he bottom of the reservoir 222. The sealed mold is then placed in a heater/oven.

Figure 21A:
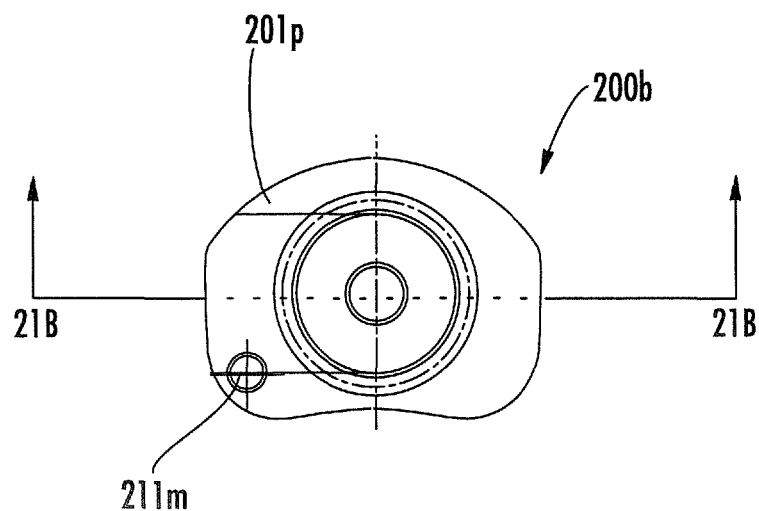
FIG. 21A is a bottom view of a bottom mold member receivable in the middle member shown in FIG. 18 according to embodiments of the present invention.
Figure 21B:
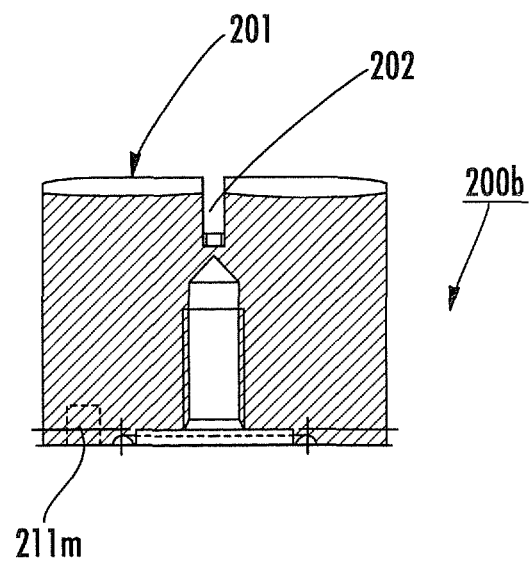
FIG. 21B is a cross-sectional view of the bottom mold member shown in FIG. 21A taken along lines 21B-21B.

FIGS. 21A and 21B illustrate an exemplary bottom mold member 200*b*. As shown, the outer perimeter shape 201*p* is substantially the same as the perimeter shape 208*p* of the middle member 208. The bottom member 200*b* defines the floor 201 shape and includes a channel 202.

Figure 22:
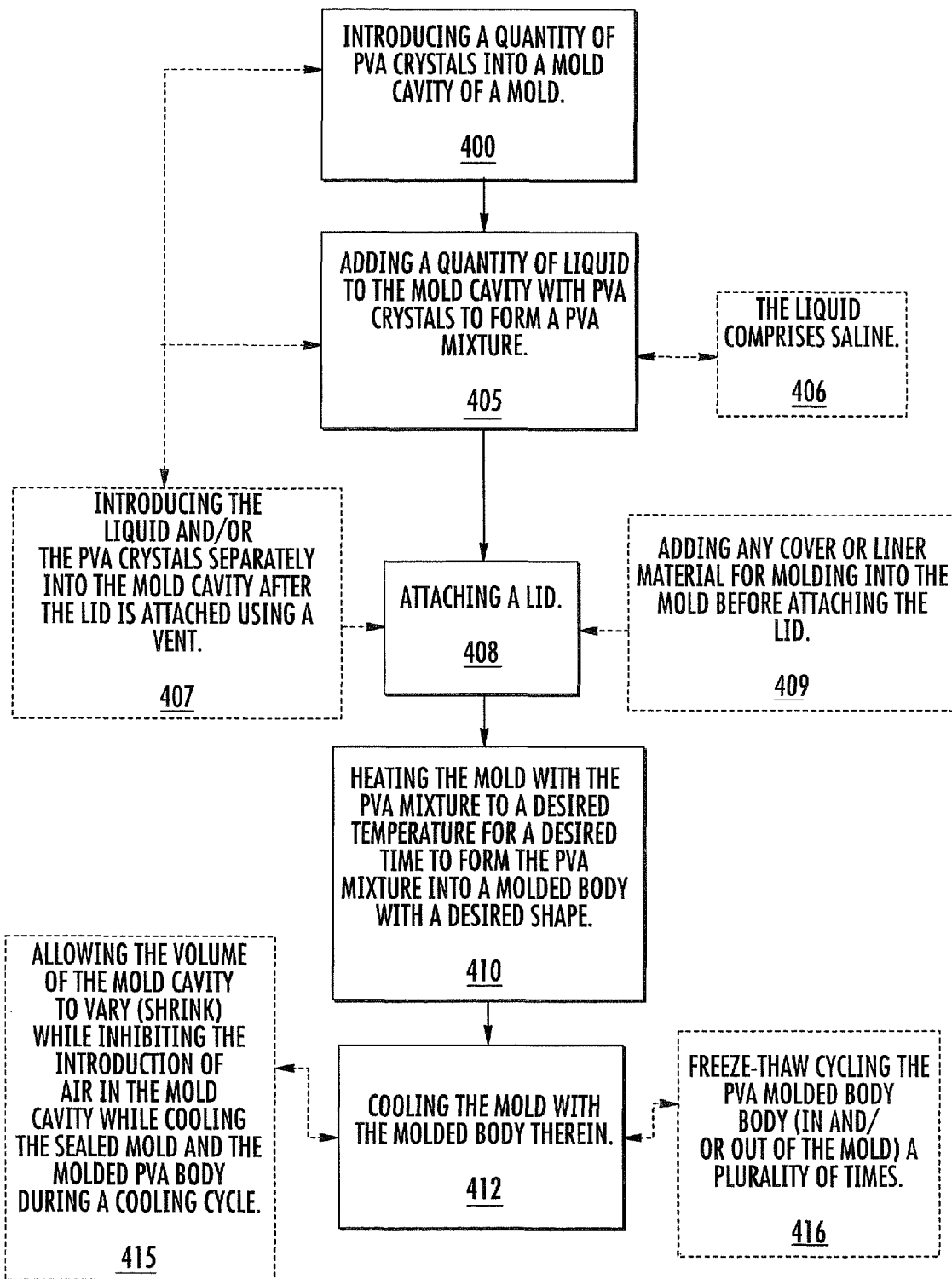
FIG. 22 is a flow chart of operations that can be used to fabricate surgical implants according to embodiments of the present invention.

FIG. 22 illustrates an exemplary fabrication process similar to that described with respect to FIG. 13 above that can be used to form any suitable implant and is not limited to spinal implants. Because the implants can be manufactured to be mechanically strong, or to possess various levels of strength among other physical properties, the process can be adapted for use in many applications. The cryogel also has a high water content, which provides desirable properties in numerous applications. For example, the cryogel tissue replacement construct is especially useful in surgical and other medical applications as an artificial material for replacing and reconstructing soft tissues or as orthopedic implants in humans and other mammals.

The fabrication process can include introducing a quantity of PVA crystals into a mold cavity (block 400). A quantity of liquid can be added to the PVA crystals to form a PVA mixture (block 405). The liquid may optionally comprise saline (block 406). Optionally, the process may also include placing one or more hydrogel inserts, produced beforehand by liquid injection of the material, in the thin areas of the mold in which the material may present a gradient of formulation at demolding (typically the skirt 14 and keel 15 sections). This can allow formation of a substantially homogeneous molded material of embedded mesh.

A mold lid is attached to substantially close the mold cavity (block 408). The liquid and/or the crystal or powder PVA material can be added independently after the lid is attached using a vent with a vent path in fluid communication with the mold cavity (block 407). The vent can be used to degas air from the mold cavity before heating, typically during evacuation of the mold cavity. The vent can be sealed before the heating step. Typically, the PVA is added before the lid is attached as well as any liner material desired (block 409) and the liquid introduced after the lid is attached. Alternatively, both the PVA and liquid can be introduced (all or portions of same) before the lid is attached. The mold cavity may become pressurized from heating the mixture in the sealed mold (a relatively high pressure is contemplated, but has not been measured).

The mold with the PVA mixture can be heated to a desired temperature for a desired time to form the PVA mixture into a molded body with a desired shape (block 410). The mold can include a dedicated interface with a thermocouple (close to mold cavity) for control of the heating step. The heating can be conducted using a band heater, substantially centered around the mold, which may reduce the length of the heating step compared to forced air convection in over. Other heating techniques may be used, such as, for example, autoclaving.

The mold with the molded body therein can be cooled after the heating (block 412). The cooling can be passive (air cooled at room temperature) or active such as forced air flow, fluid flow, refrigeration, and may include regulated temperatures or not, or the cooling can include both passive and active types of cooling.

In some embodiments, the mold cavity can be allowed to change, (typically shrink) while inhibiting the introduction of air in the mold cavity while cooling the mold and the molded PVA body (which can be held sealed therein) during a cooling cycle (block 415). As shown, for example, in FIG. 17C, the locations of the gaskets or other sealing devices 204 can maintain the seal throughout the whole cooling process (and the volume reduction of the cavity) until demolding. Demolding is typically conducted after cool down of the mold. The cooling can be any suitable type, such as, for example, natural, forced air-cooling and/or water bath and/or freezer or combinations of same. In some embodiments, the mold remains above freezing before demolding to avoid affecting the properties of the implantable device (cross-linking happens only during the subsequent thermal cycling). An exemplary temperature for demolding is above freezing and below approximately 10 degrees Celsius, such as, fore example, about 5 degrees Celsius. If the temperature is too hot, some material formulations may provide a material that is too soft to handle and its geometry may be undesirably altered. During and/or after molding, typically after demolding, the device can be processed to locally expose mesh on the endplates. After demolding, apertures (through holes) can be created in the skirt (for location of the fixation screws) and in the keel 40 (for tissue and/or bone through growth). The latter may be formed by using forming members such as pins that are maintained/held in the keel 15 through the curing (freeze-thaw) cycle(s). The forming members can be removed after the thermal cycling. The implant 10 can be hydrated, packaged, sterilized and prepared for shipment to a clinical site.

The PVA molded body can be freeze-thaw cycled (in and/or out of the mold) at least one, and typically a plurality of times (block 416). As discussed above, the moldable material can include between about 20 to about 70% (by weight) PVA powder crystals. The PVA powder crystals can have a MW of between about 124,000 to about 165,000, with about a 99.3-100% hydrolysis. The saline (irrigant or solvent) can be a solution of about 0.9% sodium chloride. The PVA crystals can be placed (dry) in the mold independently of, typically before, the irrigant (no pre-mixing is required) and/or otherwise introduced into the mold so that injection is not required. The irrigant and PVA, or just the irrigant, can be inserted into a mold after a lid is attached using a liquid vent port that can be plugged or sealed before the material and the mold are heated. After cooling, the hydrogel-molded body can be further processed without placing in water or saline during subsequent processing. The hydrogel body can be hydrated at least partially before packaging and/or before implantation. Other characteristics, features, materials or process steps for the implant fabrication can be used as described hereinabove with respect to other figures.

Soft tissue body parts, which can be replaced or reconstructed by the cryogel include, but are not limited to, vascular grafts, heart valves, esophageal tissue, skin, corneal tissue, cartilage, meniscus, and tendon. Furthermore, the cryogel may also serve as a cartilage replacement for anatomical structures including, but not limited to an ear or nose. Orthopedic implants include, but are not limited to knee, arm and hip joint replacements, load bearing surface implants and prosthetic limbs.

The cryogel may also serve as a tissue expander. Additionally, the inventive cryogel may be suitable for an implantable drug delivery device. In that application, the rate of drug delivery to tissue will depend upon cryogel pore size and degree of intermolecular meshing resulting from the freeze/thaw device. The rate of drug delivery increases with the number of pores and decreases with an increasing degree of intermolecular meshing from an increased number of freeze/thaw cycles. The cryogel may also be suitable for vascular grafts and heart valve replacements, because the cryogel is thromboresistant, and because of the particular mechanical and physiological requirements of vascular grafts when implanted into the body. The cryogel may also be used for contact lenses, as a covering for wounds such as burns and abrasions, and in other applications wherein a mechanically strong material is desired.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. An implant comprising at least one moldably attached flexible fabric keel that extends substantially upwardly and/or downwardly beyond and across at least one primary surface of the implant, wherein a respective at least one flexible keel is defined by a fold formed in a layer of fabric, the fabric attached to the implant so that the fold has a generally open elongate interior that extends across a length or width of the implant and defines a space for reinforcement.

2. An implant according to claim 1, wherein the implant is a spinal disc implant, and wherein the flexible keel comprises a mesh fabric.

3. An implant according to claim 2, wherein the flexible keel comprises a plurality of spaced apart macropores extending through the mesh substrate, the implant further comprising a reinforcement member residing in the interior of the fold open space.

4. An implant according to claim 3, wherein the macropores have a diameter of about 1mm to about 2 mm.

5. An implant according to claim 2, wherein the spinal implant has a primary body comprising crystalline PVA hydrogel, and wherein the fold extends across substantially all of at least one of the superior or inferior primary surfaces in an anterior/posterior orientation or in a lateral orientation, with a peak portion of the flexible keel residing above or below the implant primary body.

6. An implant according to claim 2, wherein the flexible keel has a height of between about 2 mm to about 10 mm, and wherein the mesh substrate has a thickness that is less than about 3 mm so that the flexible keel is thin and extends upwardly and/or downwardly from the spinal disc implant.

7. An implant according to claim 1, wherein the implant is a non-metallic spinal implant with a solid elastomeric body defining superior and inferior primary external surfaces with an annulus minor external surface therebetween, and wherein substantially all of the exterior surfaces of the implant comprises a mesh covering at least partially embedded in the solid elastomeric body, and wherein the moldably attached at least one flexible keel includes an upper and lower elongate moldably attached flexible keel that respectively extend across the superior and inferior surfaces of the spinal implant, and wherein the implant further comprises a hydrogel insert residing in the interior open space of the fold.

8. An implant according to claim 1, wherein the at least one flexible keel comprises at least one anterior-posterior keel on at least one of a superior and inferior primary surface, wherein the at least one flexible keel has a fabric thickness of between 1-2 mm and can be bent side-to-side.

9. An implant according to claim 1, wherein the at least one flexible keel comprises a single laterally extending keel extending outwardly from at least one of a superior and inferior primary surface with the fold having a loop configuration with a bendable peak portion and with upper or lower opposing edges being closely spaced apart on opposing sides of the fold and moldably attached to the implant body.

10. An implant according to claim 1, wherein the flexible keel comprises a biocompatible polyester fiber mesh material.

11. An implant according to claim 10, wherein the flexible keel is moldably attached to a solid implant body of crystalline PVA hydrogel.

12. An implant according to claim 1, wherein the flexible keel comprises polyester mesh material that is at least partially embedded with crystalline PVA hydrogel, and wherein the flexible keel can be bent relative to the body of the implant.

13. An implant according to claim 1, wherein the flexible keel is defined by a porous fabric material with a thickness of between about 0.25 mm to about 1 mm.

14. An implant according to claim 1, wherein the implant is a non-metallic total disc replacement implant that is MRI compatible.

15. An implant according to claim 14, wherein the implant is devoid of metal endplates and has a non-articulating unitary solid body of crystalline hydrogel, and wherein the spinal implant comprises a first piece of mesh material disposed about an annulus outer surface of the body having a first pore pattern, a second piece of mesh material covering at least a portion of a superior surface of the body having a second different pore pattern, and a third piece of mesh material covering at least a portion of an inferior surface of the body having the second different pore pattern, wherein the first pore pattern has a smaller pore size than the second pattern.

16. An implant according to claim 15, wherein the three pieces of mesh material substantially encase the solid body.

17. An implant according to claim 1, wherein the implant is a spinal implant with an annulus outer surface, wherein the spinal implant comprises mesh material covering that is disposed about an annulus outer surface of the spinal implant, and wherein the annulus mesh material covering has a curvilinear upper and lower perimeter shape with first and second spaced apart projecting curved segments whereby bone attachment members can extend through the projecting curved segments and into bone, and wherein the fold of the at least one flexible keel with the open center space has a length that extends across substantially all of the superior and/or inferior surface of the implant.

18. An implant according to claim 17, further comprising an osteogenic material disposed on the mesh coverings and/or directly on at least one of the annulus, superior and inferior surfaces of the solid body.

19. A method of fabricating the implant of claim 1, comprising:
placing an inferior mesh layer on a floor of a three-dimensional mold;
introducing moldable material into the mold;
placing a superior mesh layer on a top surface of the moldable material in the mold;
forming a generally outwardly extending segment with an open center space in the inferior and superior mesh layers before or during the respective placing steps to define a respective inferior and superior flexible keel;
closing the mold;
pushing any excess moldable material out of the mold in response to the closing step; and
heating the mold with the moldable material to a desired temperature so that the mold is heated to at least about 80° C. for at least about 5 minutes; then
forming a molded implant body formed by the heated moldable material whereby the mesh layers are integrally moldably attached to the molded body formed by the moldable material and the flexible mesh keels extend across respective superior and inferior surfaces of the molded body with the outwardly extending segment and open space of the inferior and superior mesh layers having an outwardly extending fold in a loop configuration to define the implant of claim 1.

20. A method according to claim 19, further comprising placing at least one hydrogel insert into the open space of the outwardly extending segment before the closing step.

21. A method according to claim 19, further comprising placing an annular mesh layer against an upstanding sidewall of the mold before the introducing step.

22. A method according to claim 19, wherein the moldable material includes PVA crystals and a liquid irrigation solution that defines a PVA hydrogel, wherein the heating is carried out to heat the mold with the moldable material to between about 80-200° C. for at least about 5 minutes to less than about 8 hours,
the method further comprising:
freezing and thawing the PVA hydrogel molded body a plurality of times after the heating to provide a crystalline implant body with a desired compressive modulus of elasticity.

23. A method according to claim 19, wherein the inferior and superior segments are fold segments, the method further comprising introducing a plurality of spaced apart pores into the fold segments of the inferior and superior mesh layers.

24. A method of fabricating an implantable total disc replacement spinal disc prosthesis, comprising:
placing an inferior mesh layer with a generally downwardly extending region on a floor of a three-dimensional mold such that a fold region of the mesh layer extends through a receiving aperture or channel in the floor;
placing an annular mesh layer against an upstanding sidewall of the mold;
introducing moldable material into the mold so that the material covers the inferior and annular mesh layers;
placing a superior mesh layer with a generally upwardly extending fold region over the moldable material;
placing a top member on the mold to close the mold; and
heating the mold with the moldable material to at least about 80° C. for a target time; then
forming the implant of claim 1 whereby the mesh layers are integrally attached to the molded body formed by the moldable material and whereby the fold regions define flexible keels on the spinal implant body that extend above and across superior and inferior surfaces of the spinal implant body.

25. A method according to claim 24, further comprising placing at least one hydrogel insert into a space defined by the respective upwardly and downwardly extending mesh layers before placing the top member on the mold.

26. A method of fabricating spinal implant, comprising:
molding an elastomeric primary body into a desired spinal implant body shape; and
moldably attaching at least one flexible fabric material keel to the molded implant body so that the at least one flexible keel extends outwardly from and across the molded implant body to form the implant of claim 1.

27. A method according to claim 26, wherein the attaching comprises forming at least one upwardly or downwardly extending fold in a flexible mesh substrate to form the at least one keel.

28. A method according to claim 26, wherein the attaching comprises molding the flexible mesh substrate to the implant body so that the fold is integrally attached to the molded implant body and extends in a desired orientation to form the at least one flexible keel.

29. A method according to claim 27, further comprising placing at least one hydrogel insert in the fold before the molding step.

30. A method according to claim 26, wherein the spinal implant is a total disc replacement implant, and wherein the at least one flexible keel extends outwardly beyond at least one of a superior or inferior primary surface thereof.

31. A method according to claim 26, wherein the spinal implant is a nucleus implant.

32. A method according to claim 27, wherein the mesh substrate comprises a polyester mesh material having a thickness that is less than about 3 mm.

* * * * *

UNITED STATES PATENT AND TRADEMARK OFFICE
CERTIFICATE OF CORRECTION

| | |
|---|---|
| PATENT NO. | : 8,603,171 B2 |
| APPLICATION NO. | : 11/626401 |
| DATED | : December 10, 2013 |
| INVENTOR(S) | : John W. McClellan, III et al. |

Page 1 of 1

It is certified that error appears in the above-identified patent and that said Letters Patent is hereby corrected as shown below:

In the Specification:

Column 9, Line 57: Please correct "21, that may"
to read -- 21 that may --

Column 9, Line 60: Please correct "21, can be"
to read -- 21 can be --

Column 9, Line 63: Please correct "extensions 21,) is"
to read -- extensions 21) is --

Signed and Sealed this
Third Day of June, 2014

Michelle K. Lee
*Deputy Director of the United States Patent and Trademark Office*